(12) United States Patent
Smith, III et al.

(10) Patent No.: US 8,957,097 B2
(45) Date of Patent: Feb. 17, 2015

(54) HEMI-PHORBOXAZOLE A DERIVATIVES AND METHODS OF THEIR USE

(75) Inventors: Amos B. Smith, III, Merion, PA (US); Zhuqing Liu, Edison, NJ (US); Anne-Marie L. Hogan, Dublin (IE); Doralyn S. Dalisay, San Diego, CA (US); Tadeusz F. Molinski, La Jolla, CA (US)

(73) Assignees: The Trustees Of The University Of Pennsylvania, Philadelphia, PA (US); The Regents Of The University Of California, Oakland, CA (US)

( * ) Notice: Subject to any disclaimer, the term of this patent is extended or adjusted under 35 U.S.C. 154(b) by 84 days.

(21) Appl. No.: 13/386,783

(22) PCT Filed: Jul. 23, 2010

(86) PCT No.: PCT/US2010/043020
§ 371 (c)(1),
(2), (4) Date: Jun. 6, 2012

(87) PCT Pub. No.: WO2011/011665
PCT Pub. Date: Jan. 27, 2011

(65) Prior Publication Data
US 2013/0030027 A1 Jan. 31, 2013

Related U.S. Application Data

(60) Provisional application No. 61/228,215, filed on Jul. 24, 2009.

(51) Int. Cl.
| | | |
|---|---|---|
| *A01N 43/76* | (2006.01) | |
| *A61K 31/42* | (2006.01) | |
| *C07D 487/00* | (2006.01) | |
| *C07D 513/00* | (2006.01) | |
| *C07D 309/00* | (2006.01) | |
| *A01N 43/90* | (2006.01) | |
| *C07D 498/22* | (2006.01) | |

(52) U.S. Cl.
CPC .............. *A01N 43/90* (2013.01); *C07D 498/22* (2013.01)
USPC ........... 514/375; 540/468; 549/357; 549/414; 549/451

(58) Field of Classification Search
None
See application file for complete search history.

(56) References Cited

U.S. PATENT DOCUMENTS

2007/0021479 A1   1/2007   Razler et al.

OTHER PUBLICATIONS

Smith et al. "Synthesis and Biological Evaluation of Phorboxazole Congeners Leading to the Discovery and Preparative-Scale Synthesis of (+)-Chlorophorboxazole A Possessing Picomolar Human Solid Tumor Cell Growth Inhibitory Activity", J.Org.Chem., 2008, vol. 73, No. 4, pp. 1201-1208.*
Dalisay et al. "Structure Elucidation at the Nanomole Scale. 2. Hemiphorboxazole A from *Phorbas* sp.", Org.Lett., published on web Apr. 2, 2009, vol. 11, No. 9, pp. 1967-1970.*
Uckun et al. "Anticancer Activity of Synthetic Analogues of the Phorboxazoles", Bioorg.Med.Chem.Lett., 2001, vol. 11, pp. 1181-1183.*
Neidle, Cancer Drug Design and Discovery, Elsevier/Academic Press, 2008, pp. 427-431.*
Ahmed et al., "Convergent synthesis of the C31 C46 domain of the phorboxazole natural products," Tetrahedron Letters, Jan. 15, 1998, 39(3-4), 183-186.

(Continued)

*Primary Examiner* — Jeffrey S Lundgren
*Assistant Examiner* — Stephanie Springer
(74) *Attorney, Agent, or Firm* — Baker & Hostetler LLP

(57) ABSTRACT

The present invention is directed to hemi phorboxazole A: and its stereoisomers, as well as derivatives of hemi phorboxazole A of formula I: wherein ring A is aryl or a 5- or 6-membered heteroaryl optionally substituted with one or more of halogen, —OH, or —$C_{1-6}$alkyl; and R is —CN, a 5- or 6-membered heteroaryl, or halogen; and the pharmaceutically acceptable salt forms thereof, in addition to methods of using these compounds.

24 Claims, No Drawings

(56) References Cited

OTHER PUBLICATIONS

Boeckman et al., "A convergent general synthetic protocol for construction of spirocyclic ketal ionophores: an application to the total synthesis of(−)-A-23187 (calcimycin)," Journal American Chemical Society, Nov. 1987, 109(24), 7553-7555.

Cory et al., "Use of an aqueous soluble tetrazolium/formazan assay for cell growth assays in culture," Cancer Communications, Jul. 1991, 3(7), 207-212.

Dalisay et al., "Structure Elucidation at the Nanomole Scale. 2. Hemi-phorboxazole A from *Phorbas* sp.," Organic Letters, May 7, 2009, 11(9), 1967-1970.

Danishefsky S., "Siloxy dienes in total synthesis," Accounts of Chemical Research B, Dec. 1981, 14(12), 400-406.

Danishefsky, S., "Cycloaddition and Cyclocondensation Reactions of Highly Functionalized Dienes: Applications to Organic Synthesis," Chemtracts Organic Chemistry, Sep./Oct. 1989, 2, 273-297.

Evans et al., "Enantioselective aldol condensations. 2. Erythro-selective chiral aldol condensations via boron enolates," Journal American Chemical Society, Apr. 1981, 103(8), 2127-2129.

International Patent Application No. PCT/US2010/043020: International Search Report dated Sep. 7, 2010, 2 pages.

Mulder et al., "Synthesis and structure—activity relationships of bengazole A analogs," Bioorganic & Medicinal Chemistry Letters, Jun. 1, 2009, 19(11), 2928-2930.

Nagao et al., "Use of chiral 1,3-oxazolidine-2-thiones in the diastereoselective synthesis of aldols," Journal Chemical Society, Chemical Communications, Jan. 1985, Issue 20, 1418-1419.

National Committee for Clinical Laboratory Standards, 2002, "Reference method for broth dilution antifungal susceptibility testing of yeast", 2nd ed. Approved standard M27-A2. National Committee for Clinical Laboratory Standards, Wayne, PA, vol. 22, No. 15, 51 pages.

Petasis et al., "Titanium-mediated carbonyl olefinations. 1. Methylenations of carbonyl compounds with dimethyltitanocene," Journal American Chemical Society, Aug. 1990, 112(17), 6392-6394.

Smith, III, et al., "(+)-Phorboxazole A Synthetic Studies. A Highly Convergent, Second generation Total Synthesis of(+)-Phorboxazole A," Organic Letters, Sep. 29, 2005, 7 (20), 4399-4402.

Smith, III, et al., "A Second-Generation Total Synthesis of (+)-Phorboxazole A ," Journal of Organic Chemistry, Feb. 15, 2008, 73(4), 1192-1200.

Smith, III, et al., "Design and Synthesis of a Potent Phorboxazole C(11-15) Acetal Analogue," Organic Letters, Feb. 16, 2006, 8(4), 797-799.

Smith, III, et al., "Total Synthesis of (+)-Phorboxazole A Exploiting the Petasis-Ferrier Rearrangement," Journal American Chemical Society, Nov. 7, 2001, 123(44), 10942-10953.

Smith, III, et al., "Total Synthesis of (+)-Phorboxazole A," Journal American Chemical Society, May 23, 2001, 123(20), 4834-4836.

Still et al., "Direct synthesis of Z-unsaturated esters. A useful modification of the horner-emmons olefination," Tetrahedron Letters, Jul. 1983, 24(41), 4405-4408.

\* cited by examiner

HEMI-PHORBOXAZOLE A DERIVATIVES AND METHODS OF THEIR USE

GOVERNMENT SUPPORT

The research carried out in this application was supported, in part, by grants from the National Institute of Health (National Cancer Institute) through grants CA-19033 and CA-122256. Pursuant to 35 U.S.C. 202, the government may have rights in any patent issuing from this application.

CROSS-REFERENCE TO RELATED APPLICATIONS

This application is the National Stage of International Application No. PCT/US2010/043020, filed Jul. 23, 2010, which claims the benefit of U.S. Provisional Application No. 61/228,215 filed Jul. 24, 2009, the disclosures of which are incorporated herein by reference in their entireties.

TECHNICAL FIELD

The present invention is directed to hemi-phorboxazole A and its derivatives, as well as methods of their use.

BACKGROUND

Phorboxazole A (1) and B (2), originally isolated from the Indian ocean sponge *Phorbas* sp., display extraordinary biological properties, including high cell growth inhibitor activity against both fungal and human tumor cell lines. For example, in vitro bioassay of 1 and 2 against the National Cancer Institute's panel of 60 human tumor cell lines revealed a mean $GI_{50}$ of $1.58 \times 10^{-9}$ M.

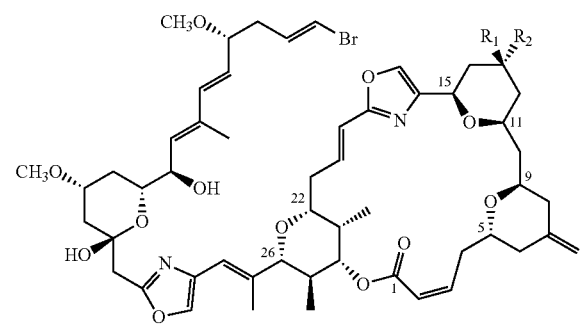

(+) Phorboxazole A (1): $R_1$ = H, $R_2$ = OH
(+) Phorboxazole B (2): $R_1$ = OH, $R_2$ = H In April 2009, the isolation of hemi-phorboxazole A (3) was reported. Dalisay, D. S.; Molinski, T. F. *Org. Lett.* 2009, 11, 1967. Hemi-phorboxazole is the first example of a natural phorboxazole variant identified since phorboxazoles A and B were first reported in 1995 and is about 10,000 times less abundant than phorboxazoles A and B (cf. 0.07 vs. 500 ppm, respectively). The limited availability of the natural material precludes any significant evaluation of its biological activity. As such, methods for the preparation of (+) hemi-phorboxazole A are needed. Moreover, to explore and maximize the biological activity of (+) hemi-phorboxazole A, synthetic analogues are needed.

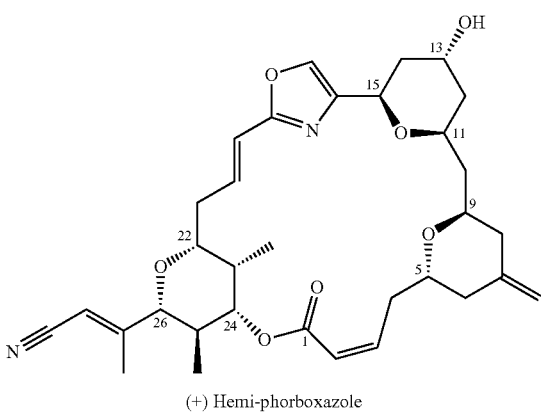

(+) Hemi-phorboxazole

SUMMARY

The present invention is directed to hemi-phorboxazole A, and its stereoisomers, and to compounds of formula I:

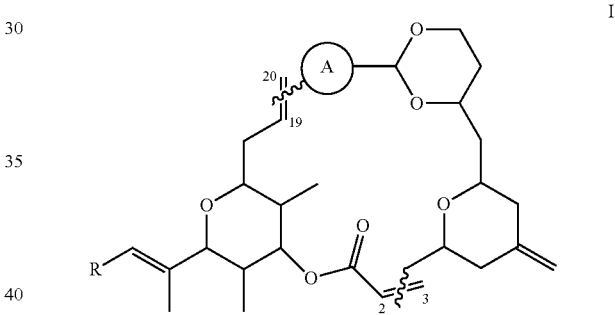

wherein ring A is aryl or a 5- or 6-membered heteroaryl optionally substituted with one or more of halogen, —OH, or —$C_{1-6}$alkyl; and R is —CN, a 5- or 6-membered heteroaryl, or halogen; as well as pharmaceutically acceptable salt forms thereof. Methods of using these compounds for the treatment of cancer or fungal infections is also described.

DETAILED DESCRIPTION OF ILLUSTRATIVE EMBODIMENTS

Amos B. Smith, III, et al. Design and Synthesis of a potent Phorboxazole C(11-15) Acetal Analogue, Org. Lett. 2006, 8(4), 797-799, the entirety of which is incorporated herein.

Amos B. Smith, III, et al. (+)-Phorboxazole A Synthetic Studies. A Highly Convergent, Second generation Total Synthesis of (+)-Phorboxazole A, Org. Lett., 2005, 7 (20) 4399-4402, the entirety of which is incorporated herein.

One embodiment of the invention is hemi-phorboxazole A, that is, a compound of the following formula wherein the stereochemistry at positions C(5), C(9), C(11), C(13), C(15), C(22), C(23), C(24), C(25) and C(26) is as shown:

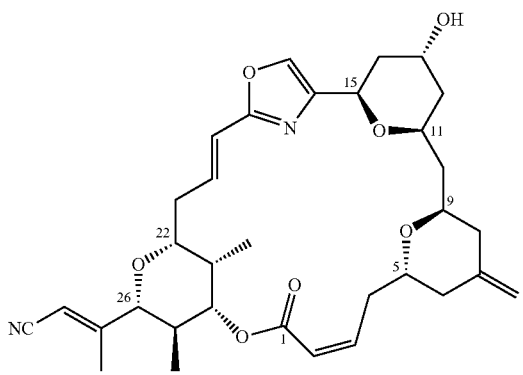

Also preferred are compounds wherein the stereochemistry at at least one of positions C(5), C(9), C(11), C(13), C(15), C(22), C(23), C(24), C(25) and C(26) is as shown:

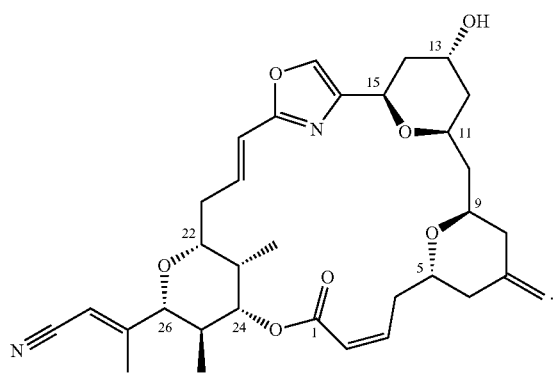 [SMILES: C=C1C[C@@H]2C[C@@H]3C[C@@H](O)C[C@@H](O3)c3coc(n3)/C=C/C[C@H]3O[C@@H](/C(C)=C/C#N)[C@H](C)[C@@H](OC(=O)/C=C\C[C@@H](C1)O2)[C@H]3C]

Also preferred are compounds wherein the stereochemistry at at least three of positions C(5), C(9), C(11), C(13), C(15), C(22), C(23), C(24), C(25) and C(26) is as shown:

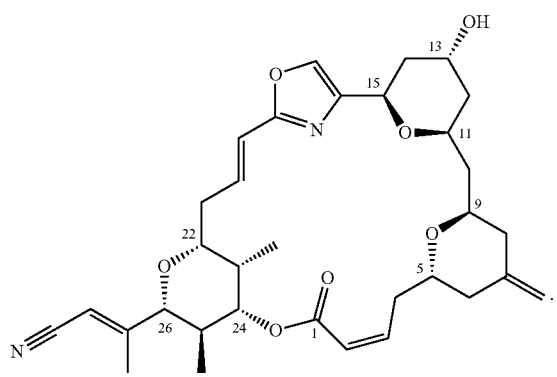 [SMILES: C=C1C[C@@H]2C[C@@H]3C[C@@H](O)C[C@@H](O3)c3coc(n3)/C=C/C[C@H]3O[C@@H](/C(C)=C/C#N)[C@H](C)[C@@H](OC(=O)/C=C\C[C@@H](C1)O2)[C@H]3C]

Also preferred are compounds wherein the stereochemistry at at least six of positions C(5), C(9), C(11), C(13), C(15), C(22), C(23), C(24), C(25) and C(26) is as shown:

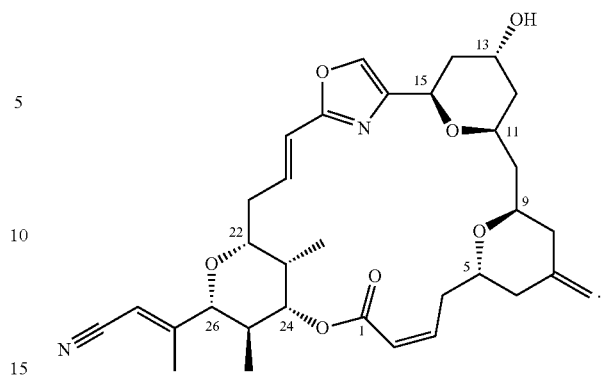

Hemi-phorboxazole A (3) was prepared in 85% yield in two steps from known compound 4. See Scheme 1. The preparation of compound 4 is described in Smith A. B., Razler, T., M., Ciavarri, J. P.; Hirose, T.; Ishikawa, T. *Org. Lett.* 2005, 7, 4399 and Smith A. B., Razler, T., M., Ciavarri, J. P.; Hirose, T.; Ishikawa, T.; Meis, R. M. *J. Org. Chem.* 2008, 73, 1192, the entireties of which are incorporated herein.

Scheme 1

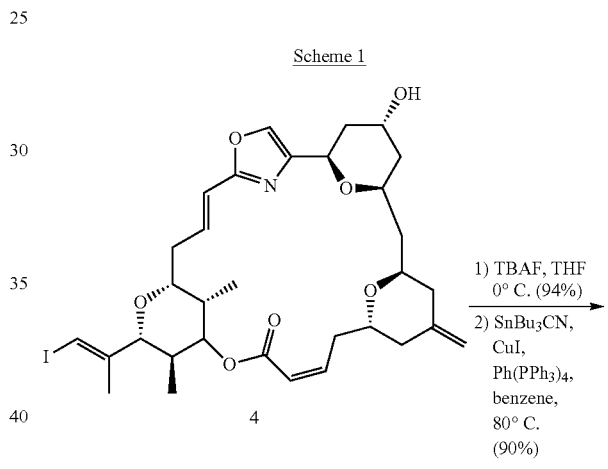

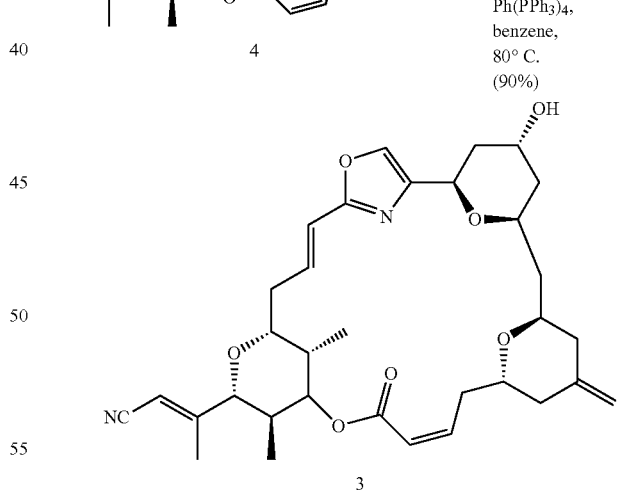

The spectral data of synthetic 3, i.e., 1D and 2D NMR, UV, circular dichromism, and high resolution mass spectroscopy, were identical in all respects with the data derived from natural hemi-phorboxazole A, thereby confirming both the complete relative stereochemistry and assigned absolute configuration.

Also within the scope of the invention are derivatives of hemi-phorboxazole A. Particularly preferred derivatives are those of formula I:

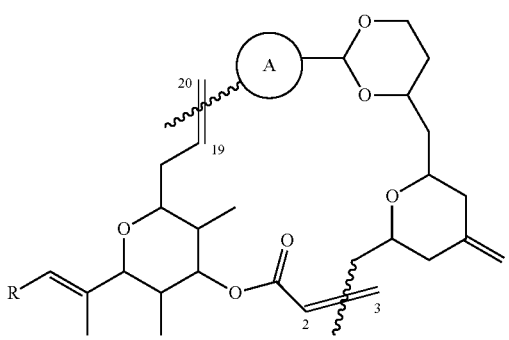

wherein ring A is aryl or a 5- or 6-membered heteroaryl; and R is —CN, a 5- or 6-membered heteroaryl, or halogen; or a pharmaceutically acceptable salt form thereof. In certain embodiment, ring A can be substituted by one or more substitutents, for example, halogen (F, Cl, Br, or I), —OH, or —$C_{1-6}$alkyl.

As used herein, the configuration

connotes that the double bond can have either the Z geometry:

or the E geometry:

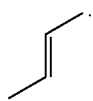

Thus, formula I encompasses the following four isomers:

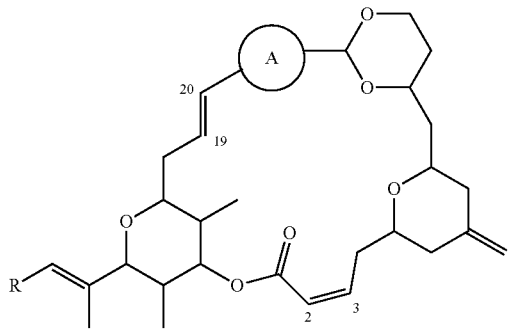

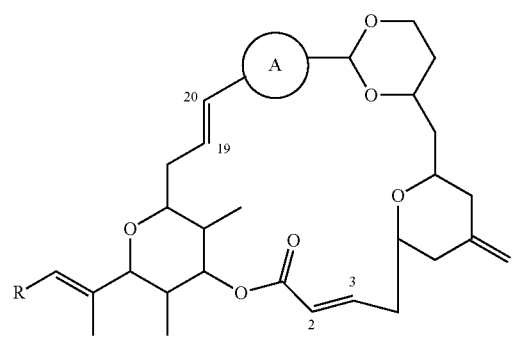

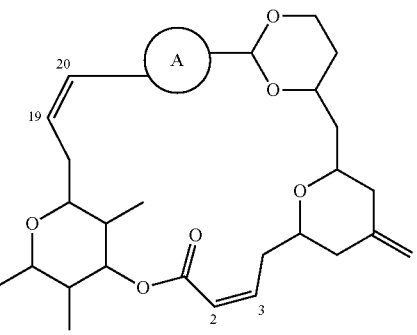

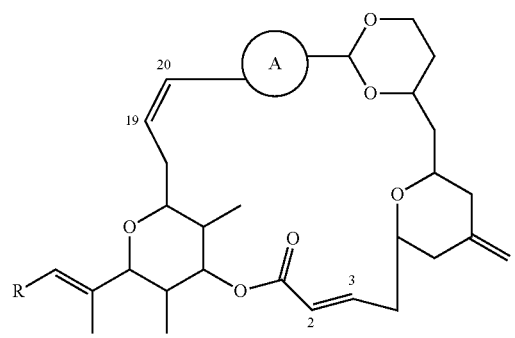

As used herein, the term "alkyl" refers to a straight-chain, or branched alkyl group having 1 to 8 carbon atoms, such as methyl, ethyl, propyl, isopropyl, butyl, isobutyl, sec-butyl, tert-butyl, pentyl, isoamyl, neopentyl, 1-ethylpropyl, 3-methylpentyl, 2,2-dimethylbutyl, 2,3-dimethylbutyl, hexyl, octyl, etc. The alkyl moiety of alkyl-containing groups has the same meaning as alkyl defined above. A designation such as "$C_1$-$C_6$ alkyl" refers to straight-chain, or branched alkyl group having 1 to 6 carbon atoms, such as methyl, ethyl, propyl, isopropyl, butyl, isobutyl, sec-butyl, tert-butyl, pentyl, isoamyl, neopentyl, 1-ethylpropyl, 3-methylpentyl, 2,2-dimethylbutyl, 2,3-dimethylbutyl, hexyl, etc. Lower alkyl groups, which are preferred, are alkyl groups as defined above which contain 1 to 4 carbons. A designation such as "$C_1$-$C_4$ alkyl" refers to an alkyl radical containing from 1 to 4 carbon atoms, such as methyl, ethyl, propyl, isopropyl, butyl, isobutyl, sec-butyl, and tert-butyl. A designation such as "$C_1$-$C_3$ alkyl" refers to an alkyl radical containing from 1 to 3 carbon atoms, such as methyl, ethyl, propyl, and isopropyl.

As used herein, "aryl" refers to monocyclic and polycyclic aromatic groups, including, for example, phenyl and naphthyl. Aryl groups may be unsubstituted or substituted with, for example, alkyl (straight- or branched-chain hydrocarbon groups containing from 1 to 6 carbon atoms, e.g., methyl, ethyl, propyl, isopropyl, butyl, and the like) and halogen (fluorine, chloride, bromine, iodine) groups.

As used herein, "heteroaryl" refers to an aryl group that contains at least one heteroatom selected from O, S, and N. Examples of heteroaryl groups include oxazolyl, pyridyl, pyrimidyl, pyrrolyl, furyl, thienyl, imidazolyl, thiazolyl, triazolyl, tetrazolyl, quinolyl, isoquinolyl, benzoimidazolyl, thiazolyl, bipyridyl, pyridylthiophenyl, pyrimidylthiophenyl, benzimidazolyl, isoxazolylthiophenyl, pyrozaolylthiophenyl, phthalimido, and benzothiazolyl. Heteroaryl groups may be unsubstituted or substituted with, for example, alkyl (straight- or branched-chain hydrocarbon groups containing from 1 to 6 carbon atoms, e.g., methyl, ethyl, propyl, isopropyl, butyl, and the like) and halogen (fluorine, chloride, bromine, iodine) groups.

In preferred embodiments, ring A is aryl. Preferably, ring A is phenyl. In other embodiments, ring A is a 5-membered heteroaryl. Preferably, ring A is oxazolyl. Also preferred are compounds wherein ring A is thiazolyl.

In some embodiments, R is —CN. In other embodiments, R is a 5- or 6-membered heteroaryl, preferably, oxazolyl or thiazolyl. In yet other embodiments, R is a halogen, preferably iodo.

In some embodiments, the geometry of the C(2-3) double bond is Z. In other embodiments, the geometry of the C(2-3) double bond is E. In some embodiments of the invention, the geometry of the C(19-20) double bond is Z. In still other embodiments, the geometry of the C(19-20) double bond is E. Preferably, the geometry of the C(2-3) double bond is Z and the geometry of the C(19-20) double bond is E. Also preferred are compounds wherein the geometry of the C(2-3) double bond is E and the geometry of the C(19-20) double bond is E. Still other preferred compounds are those wherein the geometry of the C(2-3) double bond is E and the geometry of the C(19-20) double bond is Z.

Preferred compounds of the invention include those in Table 1:

TABLE 1

| R | C(2-3), C(19-20) |
|---|---|
| —CN | (Z, E) |
| —I | (Z, E) |
| —I | (E, E) |
| —I | (E, Z) |
| —CN | (E, E) |
| —CN | (E, Z) |

TABLE 1-continued

| R | C(2-3), C(19-20) |
|---|---|
| (oxazolyl) | (Z, E) |
| (thienyl) | (Z, E) |

While all stereoisomers of the compounds of the invention are envisioned, particularly preferred compounds have the stereochemistry shown below in Table 2:

TABLE 2

| Compound No. | R | (C2-3), C(19-20) |
|---|---|---|
| (Z, E)-6 | —CN | (Z, E) |
| (Z, E)-24 | —I | (Z, E) |
| (E, E)-24 | —I | (E, E) |
| (E, Z)-24 | —I | (E, Z) |
| (E, E)-6 | —CN | (E, E) |
| (E, Z)-6 | —CN | (E, Z) |
| 27 | (oxazolyl) | (Z, E) |
| 28 | (thienyl) | (Z, E) |

Preferred compounds of the invention include those shown in Table 3:

TABLE 3

| R | C(2-3), C(19-20) |
|---|---|
| —CN | (Z, E) |
| —I | (Z, E) |
| —I | (E, E) |
| —CN | (E, E) |

While all stereoisomers of the compounds of the invention are envisioned, particularly preferred are those compounds having the stereochemistry shown below in Table 4:

TABLE 4

| Compound No. | R | C(2-3), C(19-20) |
|---|---|---|
| (Z, E)-5 | —CN | (Z, E) |
| (Z, E)-15 | —I | (Z, E) |
| (E, E)-15 | —I | (E, E) |
| (E, E)-5 | —CN | (E, E) |

Compounds of formula I can be prepared, for example, according to the sequences set forth in Schemes 2, 3, and 4 and in the Examples set forth herein. It will be appreciated by those skilled in the art that any desired stereoisomer can be obtained by modifying these procedures according to the methods known in the art. It will be appreciated by those of skill in the art that the reagents and reaction conditions set forth in the Schemes and examples are representative only and are not intended to limit the scope of the invention.

Preparation of diol 18 can be accomplished according to the sequence set forth in Scheme 2. It will be appreciated by those of skill in the art that the reagents and reaction conditions set forth in Scheme 2 are representative only and are not intended to limit the scope of the invention.

Condensation of known aldehyde 32 (Boeckman, R. K., Jr.; Charette, A. B.; Asberom, T.; Johnston, B. H. *J. Am. Chem. Soc.* 1987, 109, 7553) with the Danishefsky diene 33 ([a] Danishefsky S. *Acc Chem. Res. B* 1981, 14, 400; [b] Danishefsky, S. *Chemtracts: Org. Chem.* 1989, 2, 273)) catalyzed by Ti—(O-i-Pr)$_4$/(R)-Binol furnished the hetero-Diels-Alder adduct 34. Scandium triflate-promoted axial delivery of the TMS-thiol enol ether derived from ethylthioacetate led to trans-tetrahydropyranone 35 as a single diastereomer.

Chemoselective olefination of 35 utilizing the Petasis/Tebbe reagent (Petasis, N. A.; Bzowej, R. I. *J. Am. Chem. Soc.* 1990, 112, 6392) and 10 mol % of ethyl pivalate furnished the corresponding thiolester, which was reduced with 10% Pd/C and triethylsilane to provide aldehyde 36. The Nagao acetate aldol protocol (Nagao, Y.; Yamada, S.; Kumagai, T.; Ochiai, M.; Fujita, E. *J. Chem. Soc., Chem. Commun.* 1985, 1418), promoted by tin triflate, followed by treatment with lithium borohydride furnished diol 18.

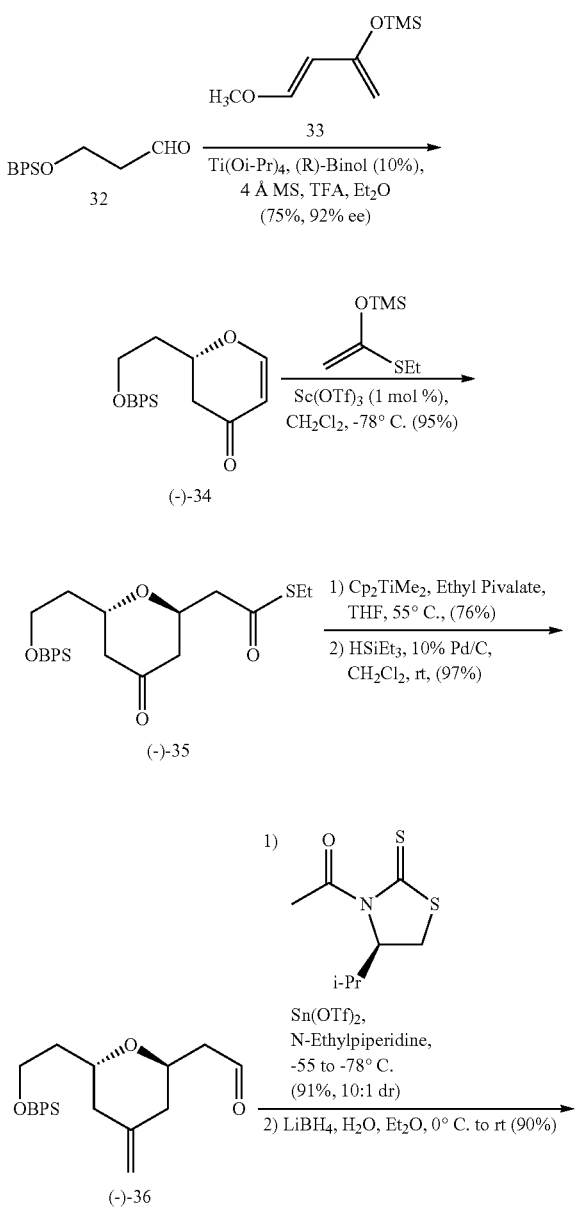

Scheme 2

-continued

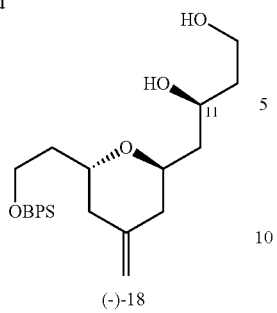

BPS = tert-butyldiphenylsilyl

Preparation of aldehyde 17 can be accomplished according to the sequence set forth in Scheme 3. It will be appreciated by those of skill in the art that the reagents and reaction conditions set forth in Scheme 3 are representative only and are not intended to limit the scope of the invention.

Construction of acid 38 began with an Evan's syn aldol (Evans, D. A.; Bartroli, J.; Shih, T. L. *J. Am. Chem. Soc.* 1981, 103, 2127), employing BPS-protected aldehyde 32, followed by hydrolysis of the resultant imide with lithium peroxide. Bis-silylation followed by TMS-OTf-promoted condensation with known aldehyde 39 (Ahmed, F.; Forsyth, C. J. *Tetrahedron Lett.* 1998, 39, 183), buffered with 2,6-di-tert-butyl-4-methylpyridine, furnished dioxanone 40. Olefination with the Petasis/Tebbe reagent, followed by exposure of the resultant enol acetal to $Me_2AlCl$ at −78° C. then led to tetrahydropyranone 41.

Kinetic enolization of ketone 41 with lithium hexamethyldisilazane (LHMDS), followed by addition of MeI furnished the equatorial methyl ketone. Axial hydride delivery employing sodium borohydride, followed by protection of the resultant equatorial alcohol with 3,4-dimethoxybenzyl chloride led to 42. The BPS protecting group was removed with tetra butyl ammonium fluoride (TBAF), followed by Parikh-Doering oxidation that provided aldehyde 17.

Scheme 3

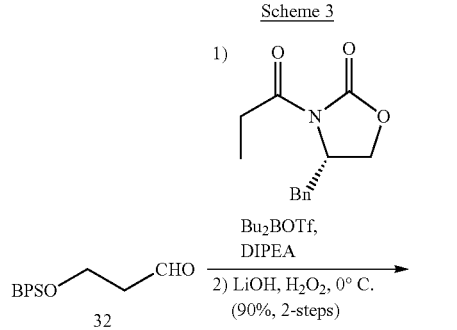

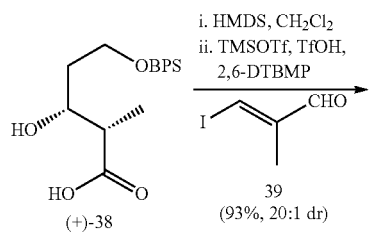

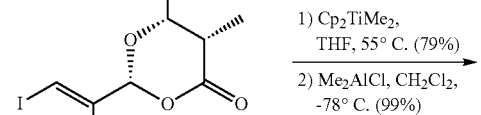

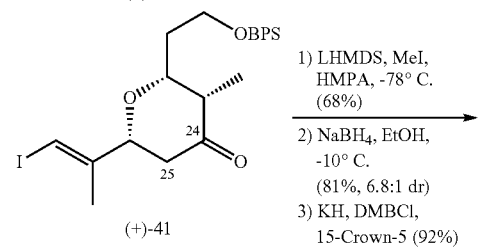

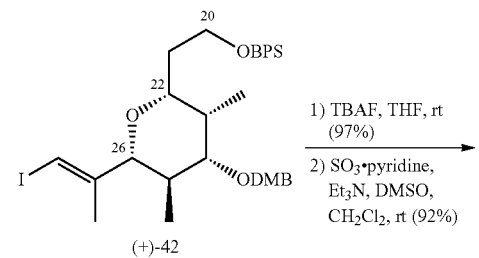

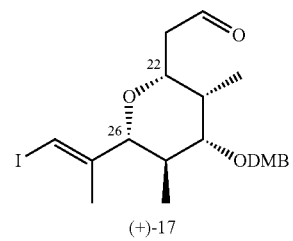

With compounds 17 and 18 in hand, compounds of formula I can be prepared. Preparation of compounds of formula I can be accomplished according to the sequence set forth in Scheme 4. It will be appreciated by those of skill in the art that the reagents and reaction conditions set forth in Scheme 4 are representative only and are not intended to limit the scope of the invention.

Condensation of diol 18 and an aldehyde of formula 143, employing dehydrating conditions, provides cis-acetal 144. Removal of the p-methoxybenzyl group at C(19) and exposure of the resultant primary alcohol to mesyl chloride and disopropylethylamine provides mesylate 145. Alternatively, the primary alcohol can be treated with $CCl_4$ and $PPh_3$ to provide the corresponding chloride. Treatment of the mesylate with tributyl phosphine can be followed by introduction of aldehyde 17 and DBU to form the E-olefin 146. Hydroxy aldehyde 147 can be obtained via a three-step sequence: removal of the silyl ether at C(3), Dess-Martin oxidation of the resultant primary alcohol to the corresponding aldehyde, and DDQ mediated generation of the secondary hydroxyl at C(24). Macrocyclization of 147 to form macrolide 115 can be achieved by employing a Still-Genari modified Horner-Emmons olefination (Still, W. C.; Gennari, C *Tetrahedron Lett.* 1983, 24, 4405). Palladium-catalyzed cyanation of vinyl iodide 115 can produce a compound of formula I.

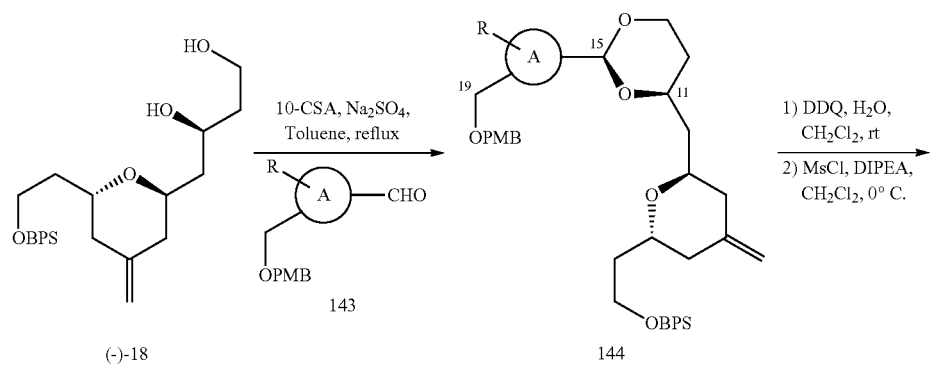
Scheme 4
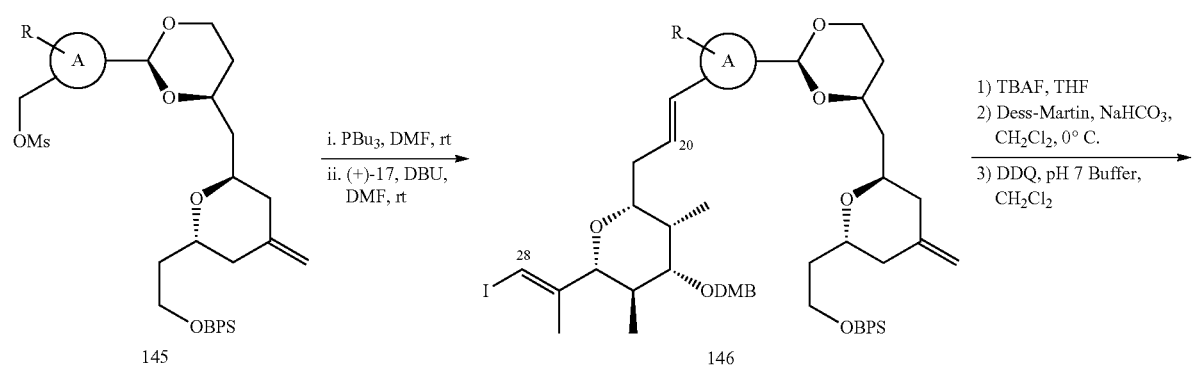
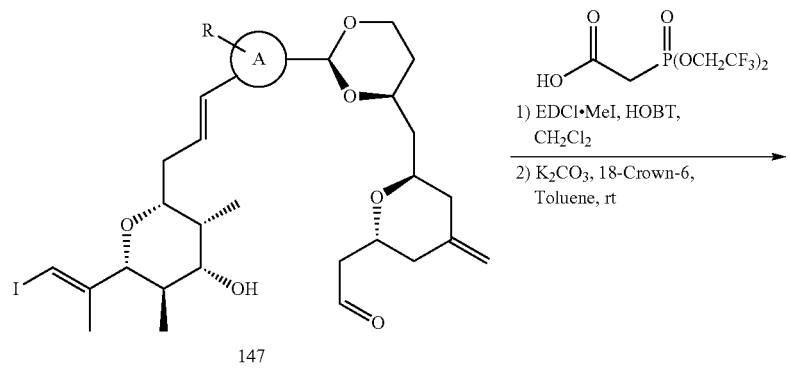

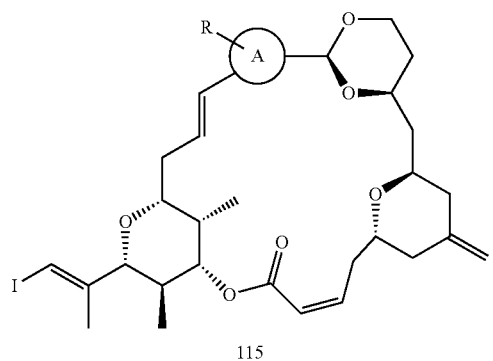

115

R = one or more halogen, C$_{1-6}$alkyl, or —OH

-continued

SnBu$_3$CN
Pd(PPh$_3$)$_4$, CuI
─────────────────
Benzene, 80° C.

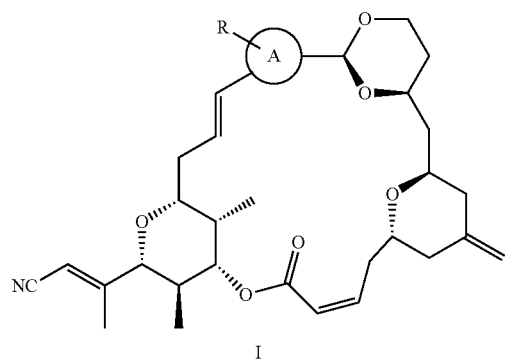

I

Within the scope of the invention are compounds of formula I, wherein ring A is oxazolyl:

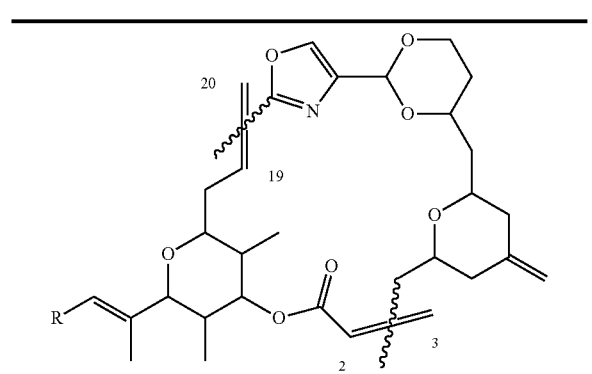

| R | C(2-3), C(19-20) |
|---|---|
| —CN | (Z, E) |
| —I | (Z, E) |
| —I | (E, E) |
| —CN | (E, E) |

While all possible stereoisomers are envisioned as within the scope of the invention, particularly preferred are those compounds wherein the stereochemistry at at least one of positions C(5), C(9), C(11), C(15), C(22), C(23), C(24), C(25) and C(26) is as shown:

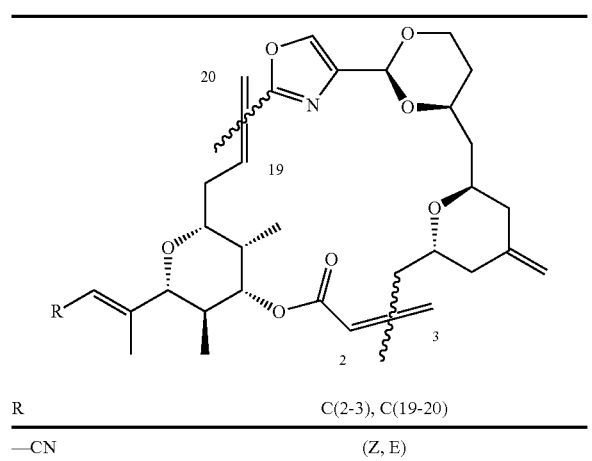

| R | C(2-3), C(19-20) |
|---|---|
| —CN | (Z, E) |
| —I | (Z, E) |

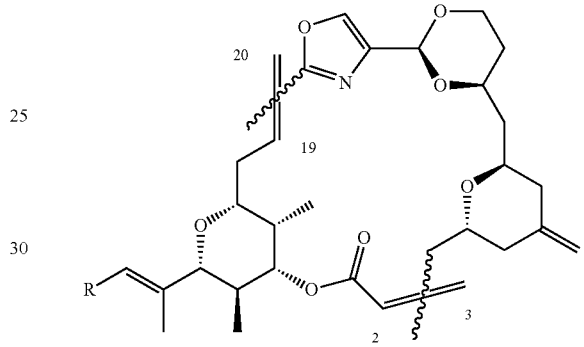

| R | C(2-3), C(19-20) |
|---|---|
| —I | (E, E) |
| —CN | (E, E) |

Even more preferred are compounds wherein the stereochemistry at positions C(5), C(9), C(11), C(15), C(22), C(23), C(24), C(25) and C(26) is as shown:

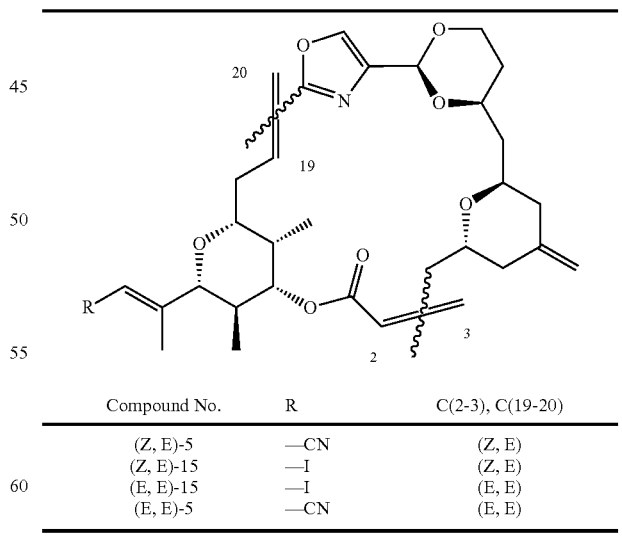

| Compound No. | R | C(2-3), C(19-20) |
|---|---|---|
| (Z, E)-5 | —CN | (Z, E) |
| (Z, E)-15 | —I | (Z, E) |
| (E, E)-15 | —I | (E, E) |
| (E, E)-5 | —CN | (E, E) |

Compounds of formula I wherein ring A is oxazolyl, for example, compound 5, can be prepared according the methods described herein and as set forth in Scheme 5. It will be appreciated by those of skill in the art that the reagents and reaction conditions set forth in Scheme 5 are representative only and are not intended to limit the scope of the invention.

Scheme 5
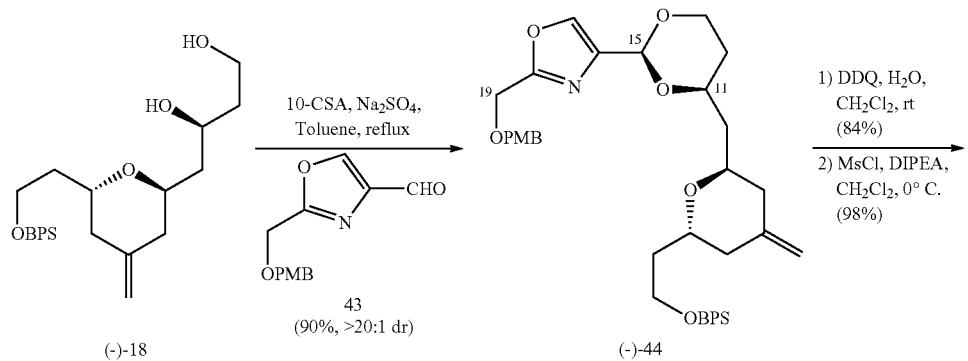
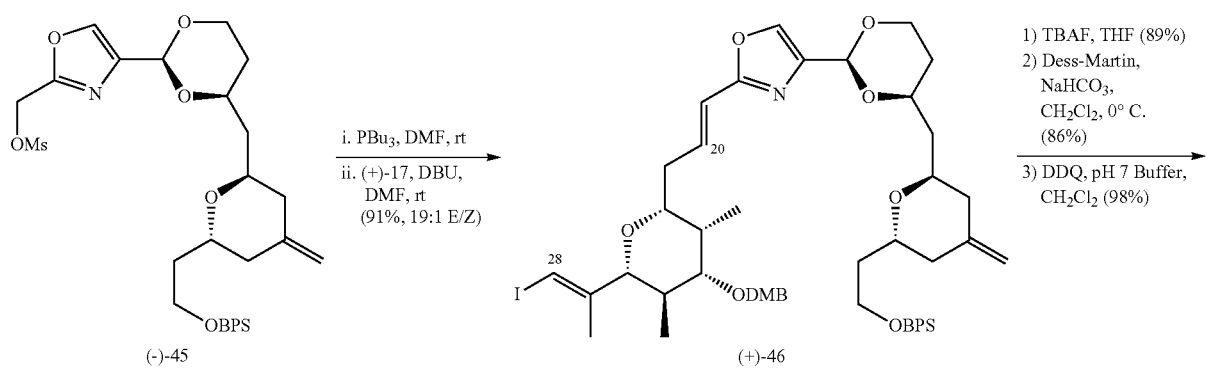
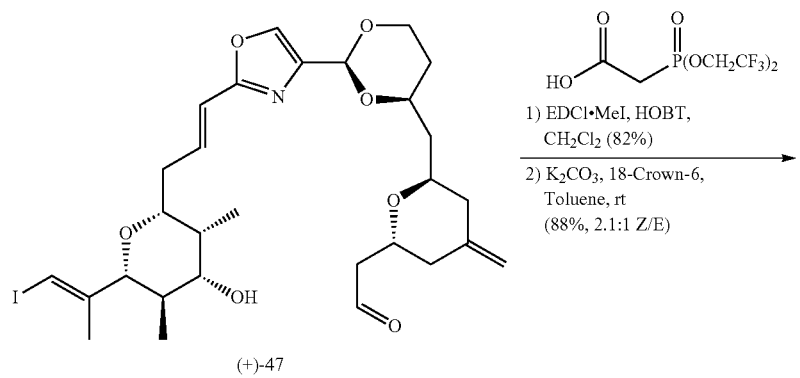

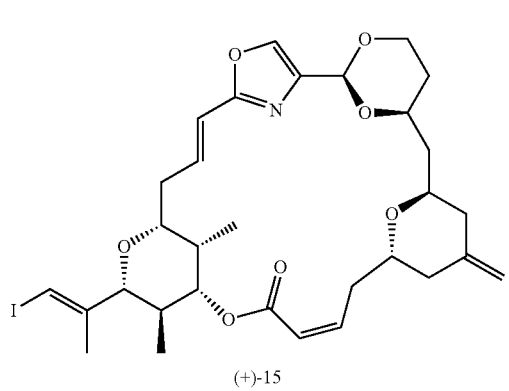 (+)-15

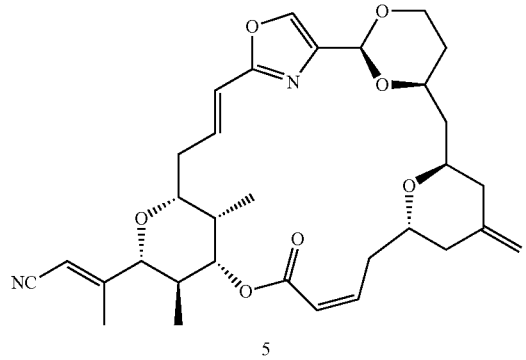 5

SnBu₃CN, Pd(PPh₃)₄, CuI, Benzene, 80° C. (90%)

Also within the scope of the invention are compounds of formula I, wherein ring A is phenyl:

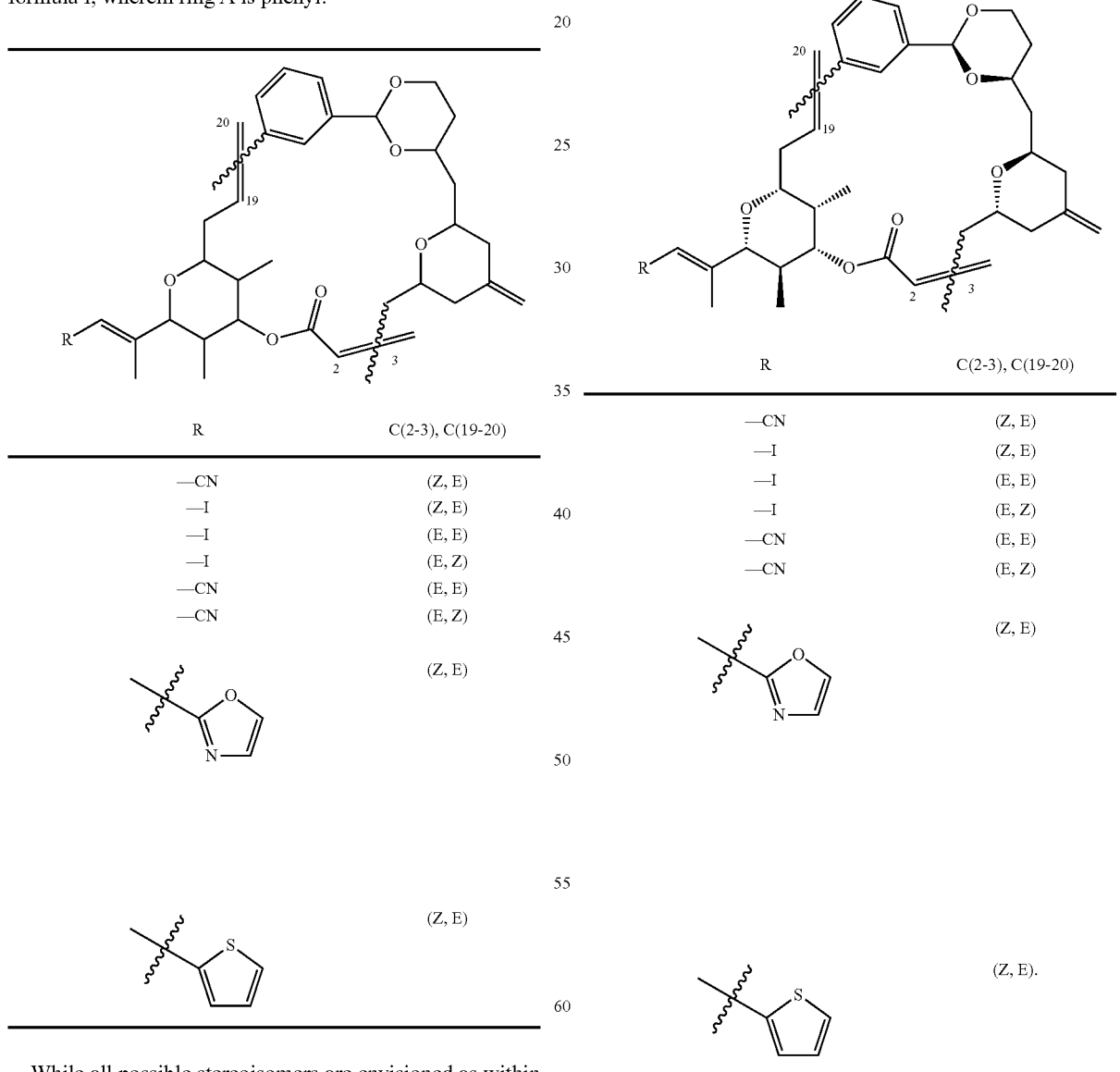

| R | C(2-3), C(19-20) |
|---|---|
| —CN | (Z, E) |
| —I | (Z, E) |
| —I | (E, E) |
| —I | (E, Z) |
| —CN | (E, E) |
| —CN | (E, Z) |
| oxazolyl | (Z, E) |
| thienyl | (Z, E) |

| R | C(2-3), C(19-20) |
|---|---|
| —CN | (Z, E) |
| —I | (Z, E) |
| —I | (E, E) |
| —I | (E, Z) |
| —CN | (E, E) |
| —CN | (E, Z) |
| oxazolyl | (Z, E) |
| thienyl | (Z, E). |

While all possible stereoisomers are envisioned as within the scope of the invention, particularly preferred are those compounds wherein the stereochemistry at at least one of positions C(5), C(9), C(11), C(15), C(22), C(23), C(24), C(25) and C(26) is as shown:

Even more preferred are compounds wherein the stereochemistry at positions C(5), C(9), C(11), C(15), C(22), C(23), C(24), C(25) and C(26) is as shown:

21

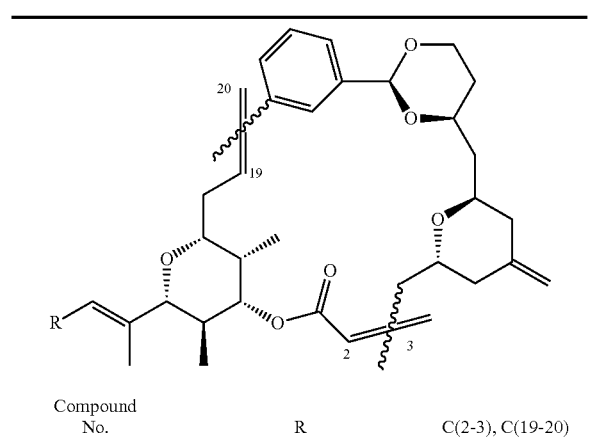

| Compound No. | R | C(2-3), C(19-20) |
|---|---|---|
| (Z, E)-6 | —CN | (Z, E) |
| (Z, E)-24 | —I | (Z, E) |
| (E, E)-24 | —I | (E, E) |
| (E, Z)-24 | —I | (E, Z) |

22

-continued

| | | |
|---|---|---|
| (E, E)-6 | —CN | (E, E) |
| (E, Z)-6 | —CN | (E, Z) |
| 27 | 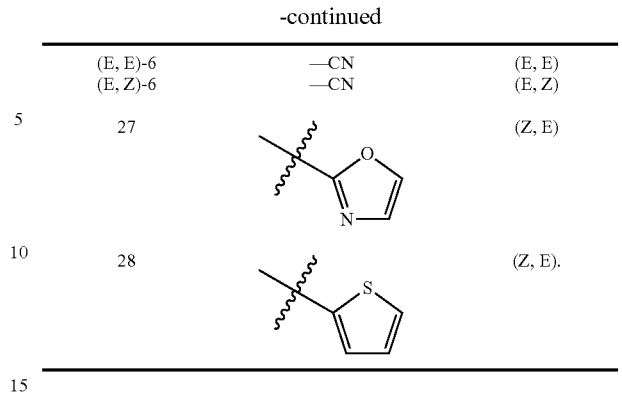 | (Z, E) |
| 28 | | (Z, E). |

Compounds of formula I wherein ring A is phenyl, for example, compound 6, can be prepared according the methods described herein and as set forth in Scheme 6. It will be appreciated by those of skill in the art that the reagents and reaction conditions set forth in Scheme 6 are representative only and are not intended to limit the scope of the invention.

Scheme 6

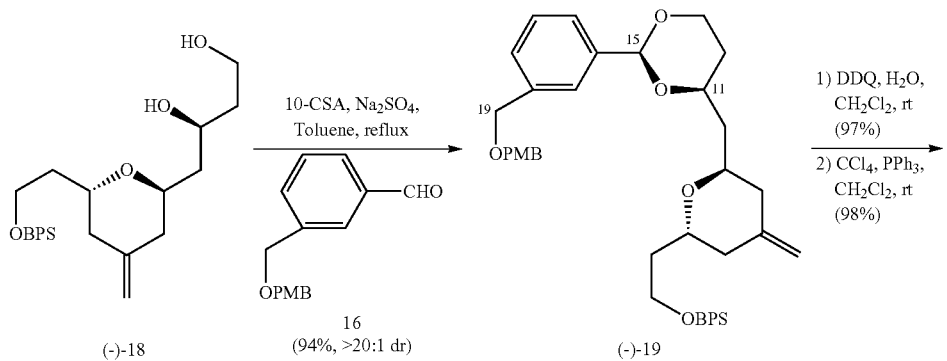

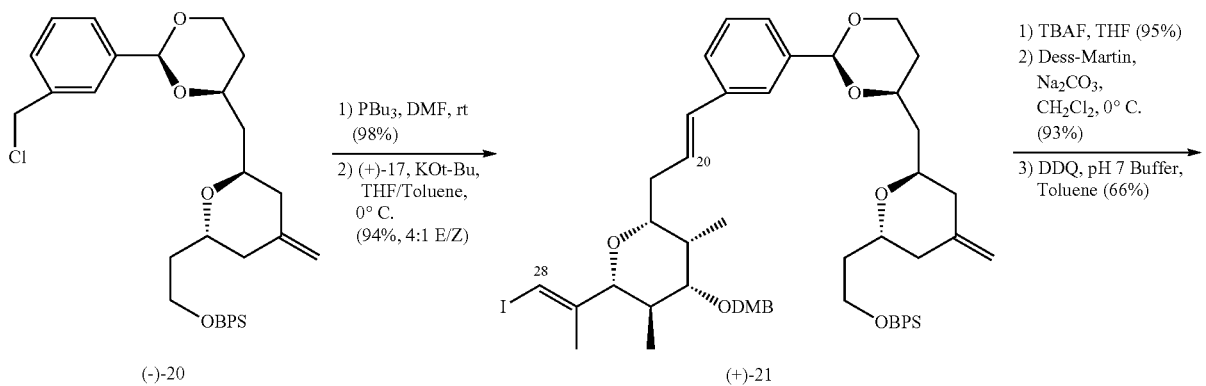

-continued
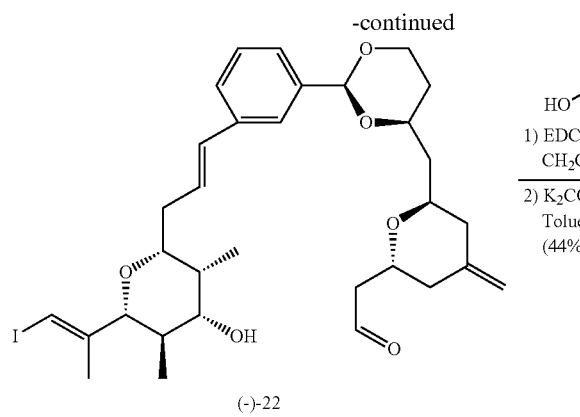
(-)-22
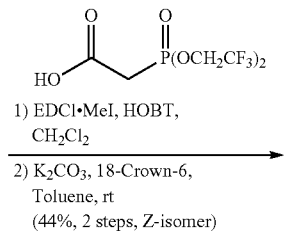
1) EDCl·MeI, HOBT, CH$_2$Cl$_2$
2) K$_2$CO$_3$, 18-Crown-6, Toluene, rt
(44%, 2 steps, Z-isomer)
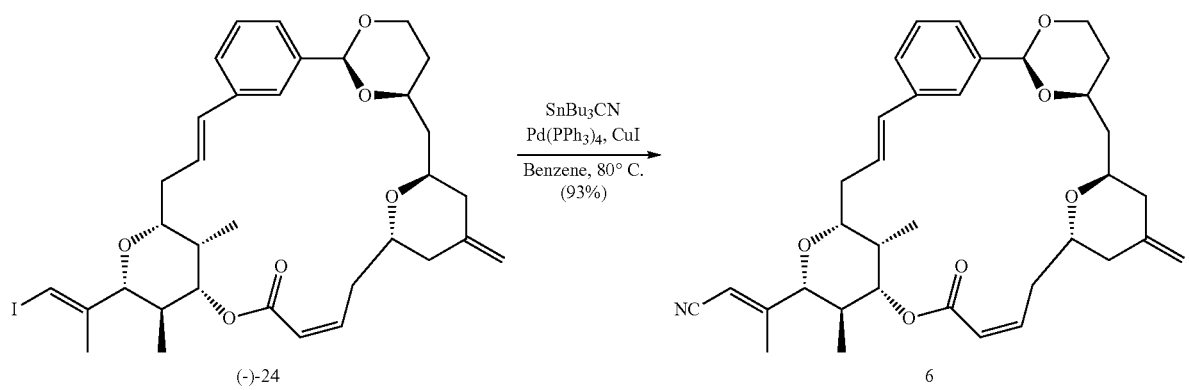
(-)-24 → 6
SnBu$_3$CN
Pd(PPh$_3$)$_4$, CuI
Benzene, 80° C.
(93%)
Biological Data
Compounds of the invention were assayed for tumor cell growth inhibitory activity, in parallel with (+) phorboxazole A (1) hemi-phorboxazole A (3). See Tables 5 and 6.
TABLE 5
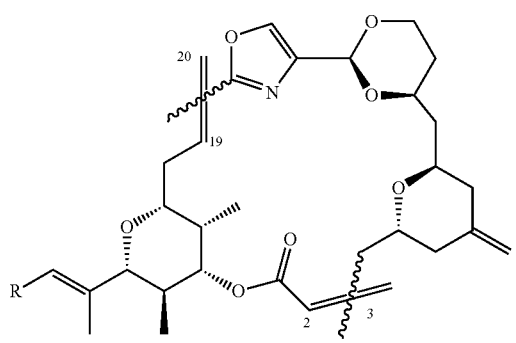
| Comp. No. | R | [C(2-3), C(19-20)] | HCT-116 Colon | SK-BR-3 Breast |
|---|---|---|---|---|
| (Z, E)-5 | —CN | (Z, E) | >6200 | >6200 |
| (Z, E)-15 | —I | (Z, E) | >6250 | |
| (E, E)-15 | —I | (E, E) | >6250 | |
| (E, E)-5 | —CN | (E, E) | 1540 | |

TABLE 5-continued
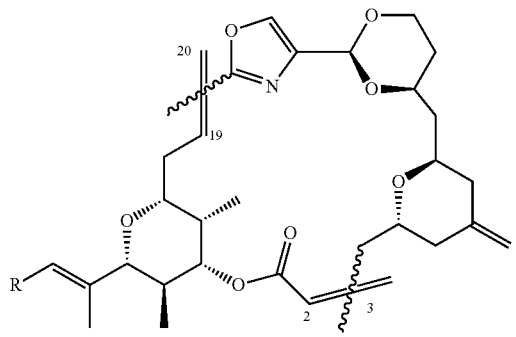
| Comp. No. | R | [C(2-3), C(19-20)] | HCT-116 Colon | SK-BR-3 Breast |
|---|---|---|---|---|
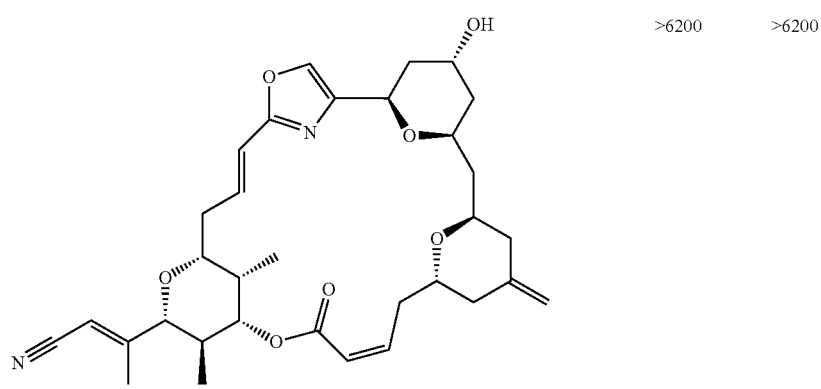
>6200   >6200
HEMI-PHORBOXAZOLE A
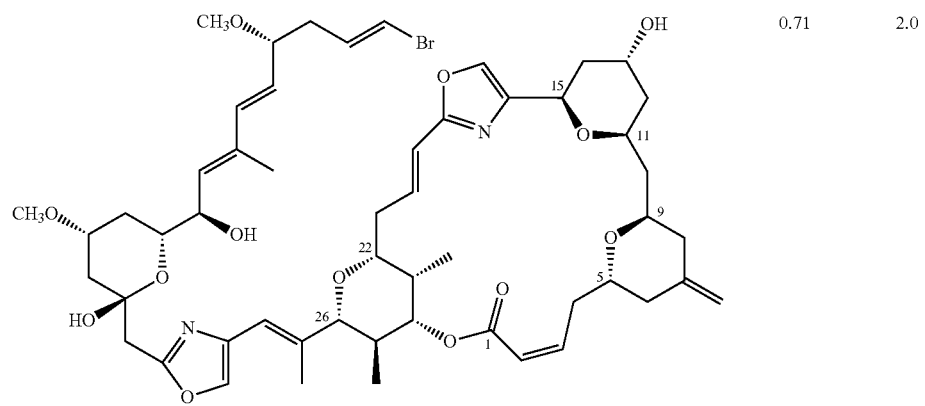
0.71   2.0
Phorboxazole A
$^a$IC$_{50}$ = ng/mL TABLE 6
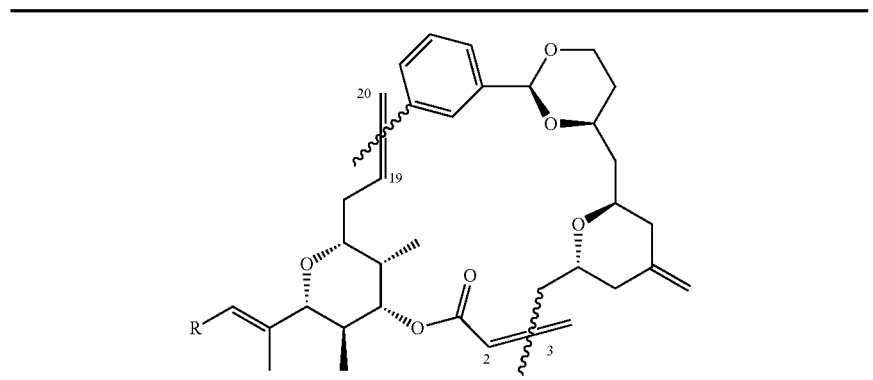
| Comp. No. | R | [C(2-3), C(19-20)] | HCT-116 Colon[a] | SK-BR-3 Breast[a] |
|---|---|---|---|---|
| (Z, E)-6 | —CN | (Z, E) | 207 | 258 |
| (Z, E)-24 | —I | (Z, E) | >6250 | |
| (E, E)-24 | —I | (E, E) | >6250 | |
| (E, Z)-24 | —I | (E, Z) | >6250 | |
| (E, E)-6 | —CN | (E, E) | >6250 | |
| (E, Z)-6 | —CN | (E, Z) | >6250 | |
| 27 | 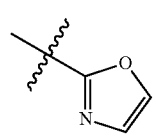 [SMILES: *c1ncco1] | (Z, E) | 5440 | |
| 28 | 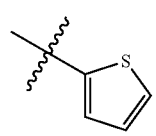 [SMILES: *c1cccs1] | (Z, E) | 5960 | |
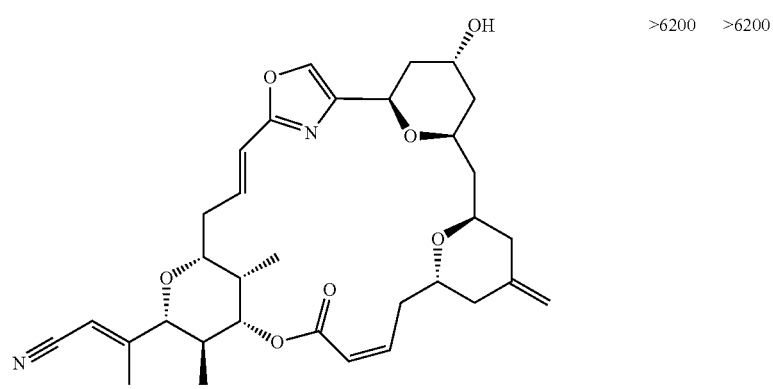
HEMI-PHORBOXAZOLE A
>6200  >6200

TABLE 6-continued

| Comp. No. | R | [C(2-3), C(19-20)] | HCT-116 Colon[a] | SK-BR-3 Breast[a] |
|---|---|---|---|---|
| Phorboxazole A | | | 0.71 | 2.0 |

[a]$IC_{50}$ = ng/mL

Tests of antifungal activity in microbroth dilution assay against pathogenic *Candida* strains was performed according to known methods. (National Committee for Clinical Laboratory Standards, 2002. Reference method for broth dilution antifungal susceptibility testing of yeast, 2nd ed. Approved standard M27-A2. National Committee for Clinical Laboratory Standards, Wayne, Pa.). For strains see: Mulder, R. J.; Shafer, C. M.; Dalisay, D. S.; Molinski, T. F. *Bioorg. Med. Chem. Lett.* 2009, 19, 2928-2930. See Tables 7 and 8.

TABLE 7

| | | | C. albicans | | |
|---|---|---|---|---|---|
| Comp. No | R | [C(2-3), C(19-20)] | ACTCC 14503[b] | UCD-FR1[b] | 96-489[b] |
| (Z, E)-5 | —CN | (Z, E) | 16 | 16 | >64 |
| (Z, E)-15 | —I | (Z, E) | >64 | >64 | >64 |
| (E, E)-15 | —I | (E, E) | >64 | >64 | >64 |

TABLE 7-continued
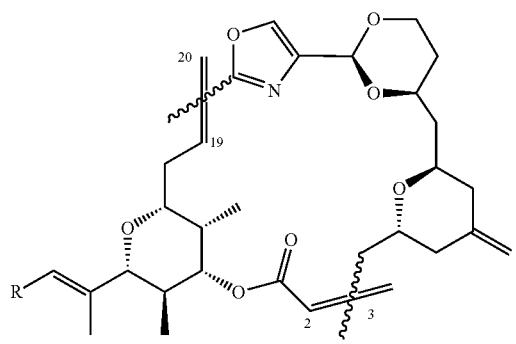
| Comp. No | R | [C(2-3), C(19-20)] | C. albicans ATCC 14503[b] | UCD-FR1[b] | 96-489[b] |
|---|---|---|---|---|---|
| (E, E)-5 | —CN | (E, E) | 4 | 8 | 32 |
| | | | >64 | >64 | >64 |
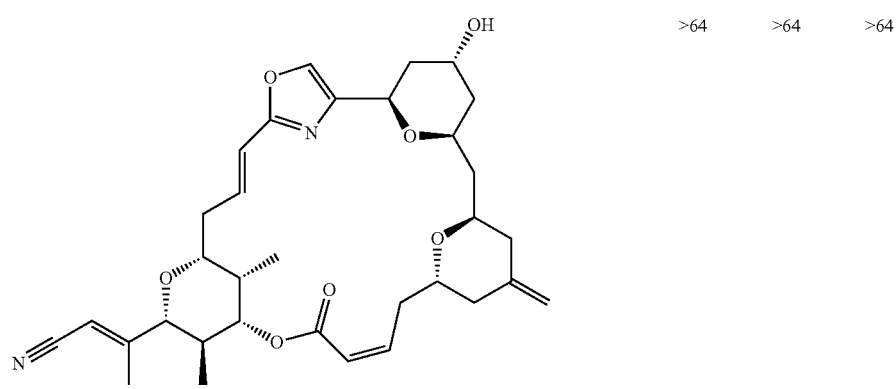
HEMI-PHORBOXAZOLE A
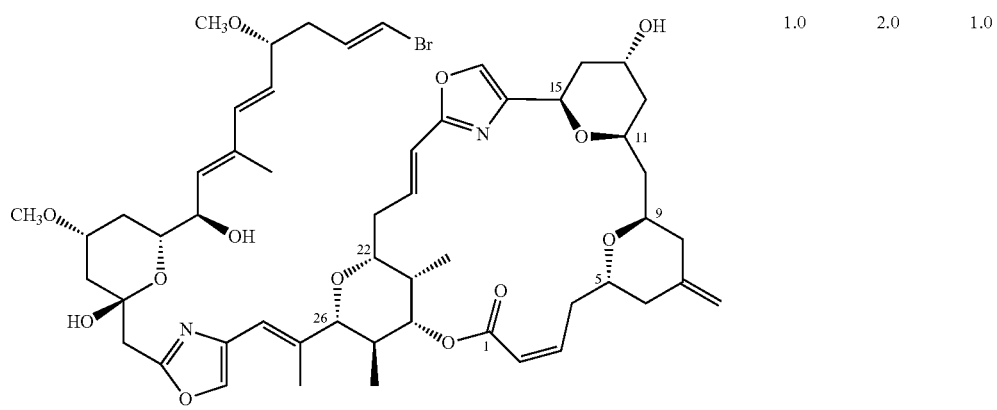
Phorboxazole A
1.0  2.0  1.0
[b]MIC, μg/mL TABLE 8
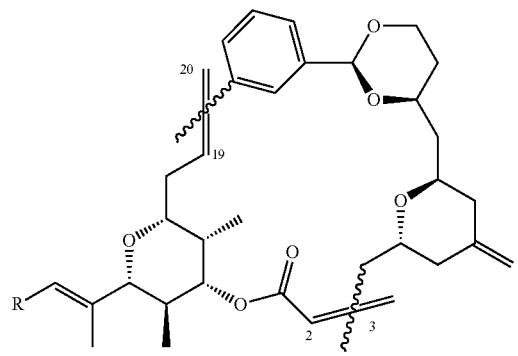
| Comp. No. | R | [C(2-3), C(19-20)] | C. albicans ACTCC 14503[b] | UCD-FR1[b] | 96-489[b] |
|---|---|---|---|---|---|
| (Z, E)-6 | —CN | (Z, E) | — | — | — |
| (Z, E)-24 | —I | (Z, E) | >64 | >64 | >64 |
| (E, E)-24 | —I | (E, E) | >64 | >64 | >64 |
| (E, Z)-24 | —I | (E, Z) | >64 | >64 | >64 |
| (E, E)-6 | —CN | (E, E) | >64 | >64 | >64 |
| (E, Z)-6 | —CN | (E, Z) | >64 | >64 | >64 |
| 27 | 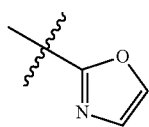 [SMILES: *c1ncco1] | (Z, E) | 4 | 8 | 32 |
| 28 | 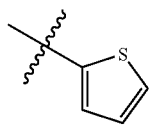 [SMILES: *c1cccs1] | (Z, E) | 8 | 16 | 32 |
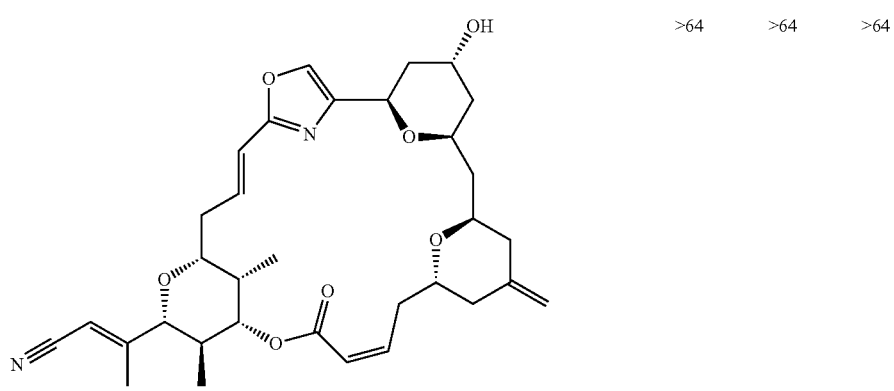
HEMI-PHORBOXAZOLE A
>64   >64   >64

TABLE 8-continued

| | | | C. albicans | | |
|---|---|---|---|---|---|
| Comp. No. | R | [C(2-3), C(19-20)] | ACTCC 14503[b] | UCD-FR1[b] | 96-489[b] |
| | Phorboxazole A | | 1.0 | 2.0 | 1.0 |

[b]MIC, µg/mL

In view of the foregoing, compounds of formula I are useful for the treatment of cancer, for example colon cancer or breast cancer, in a patient. These methods comprising administering to the patient a therapeutically effective amount of a compound of formula I.

Compounds of formula I are also envisioned as being useful in the treatment of fungal infections, in particular, fungal infections resulting from *Candida albicans*. These methods comprising administering to the patient a therapeutically effective amount of a compound of formula I.

Also within the scope of the invention are pharmaceutical compositions comprising hemi phorboxazole A and at least one pharmaceutically acceptable carrier or diluent. Pharmaceutical compositions comprising a compound of formula I and at least one pharmaceutically acceptable carrier or diluent are also envisioned.

As used herein, a "therapeutically effective amount" refers to an amount of a compound of the present invention effective to prevent or treat the symptoms of a particular disorder.

As used herein, the term "patient" refers to a warm blooded animal such as a mammal, preferably a human, or a human child, that is afflicted with, or has the potential to be afflicted with one or more diseases and conditions described herein.

As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

Within the scope of the invention are compounds of the following formula:

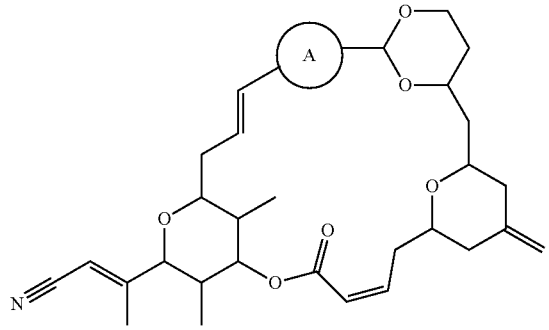

wherein ring A is aryl or a 5- or 6-membered heteroaryl; as well as the pharmaceutically acceptable salt forms thereof. In some embodiments ring A is aryl, preferably phenyl. In other embodiments, ring A is a 5-member heteroaryl, preferably oxazolyl or thiazolyl.

Preferred compounds of the invention are of the following formula:

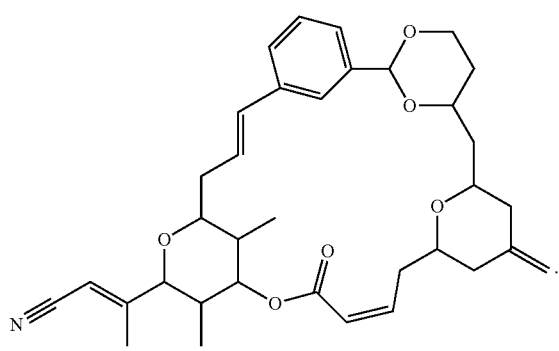 [SMILES: C=C1CC2C/C=C\C(=O)OC3C(C)C(C/C=C/c4cccc(c4)C4OCCC(CC(C1)O2)O4)OC(/C(C)=C/C#N)C3C]

In preferred embodiments, the stereochemistry at at least one of positions C(5), C(9), C(11), C(15), C(22), C(23), C(24), C(25) and C(26) is as shown below:

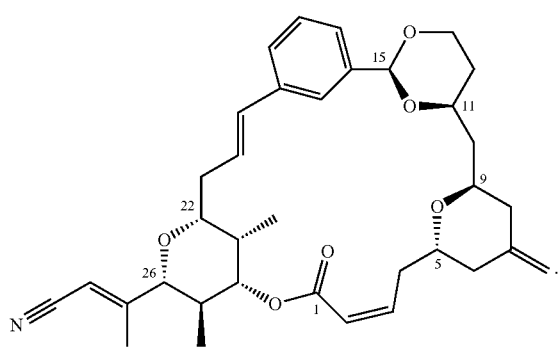 [SMILES: C=C1C[C@@H]2C[C@@H]3CCO[C@@H](O3)c3cccc(c3)/C=C/C[C@H]3O[C@@H](/C(C)=C/C#N)[C@H](C)[C@@H](OC(=O)/C=C\C[C@@H](C1)O2)[C@H]3C]

More preferably, the stereochemistry at positions C(5), C(9), C(11), C(15), C(22), C(23), C(24), C(25) and C(26) is as shown below:

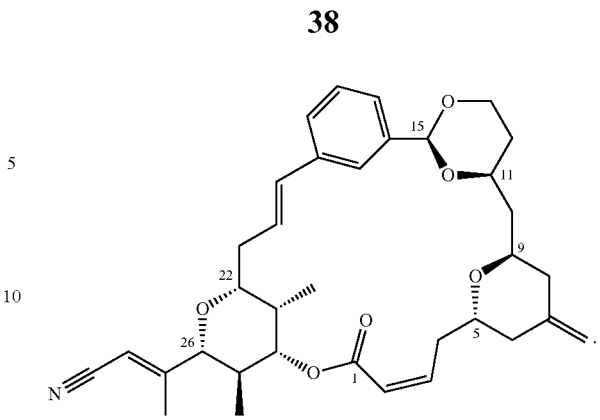

Other preferred compounds of the invention are of the following formula:

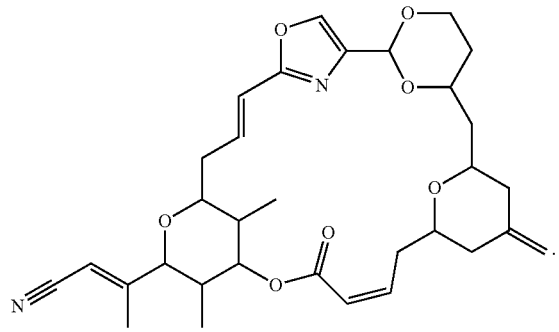 [SMILES: C=C1CC2C/C=C\C(=O)OC3C(C)C(C/C=C/c4nc(co4)C4OCCC(CC(C1)O2)O4)OC(/C(C)=C/C#N)C3C]

Preferably, the stereochemistry at at least one of positions C(5), C(9), C(11), C(15), C(22), C(23), C(24), C(25) and C(26) is as shown below:

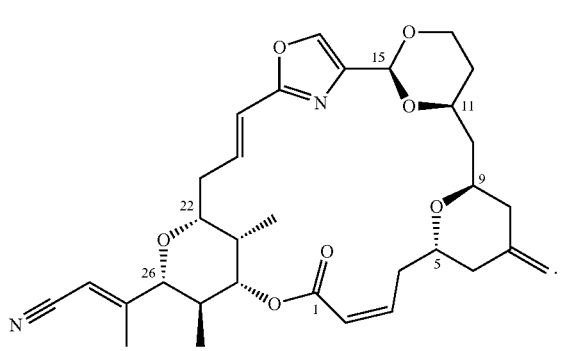 [SMILES: C=C1C[C@@H]2C[C@@H]3CCO[C@@H](O3)c3coc(n3)/C=C/C[C@H]3O[C@@H](/C(C)=C/C#N)[C@H](C)[C@@H](OC(=O)/C=C\C[C@@H](C1)O2)[C@H]3C]

More preferably, the stereochemistry at positions C(5), C(9), C(11), C(15), C(22), C(23), C(24), C(25) and C(26) is as shown below:

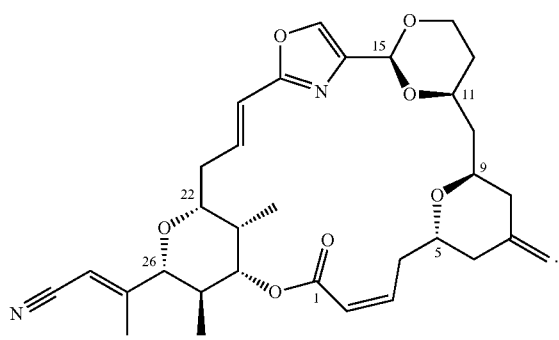 [SMILES: C=C1C[C@@H]2C[C@@H]3CCO[C@@H](O3)c3coc(n3)/C=C/C[C@H]3O[C@@H](/C(C)=C/C#N)[C@H](C)[C@@H](OC(=O)/C=C\C[C@@H](C1)O2)[C@H]3C]

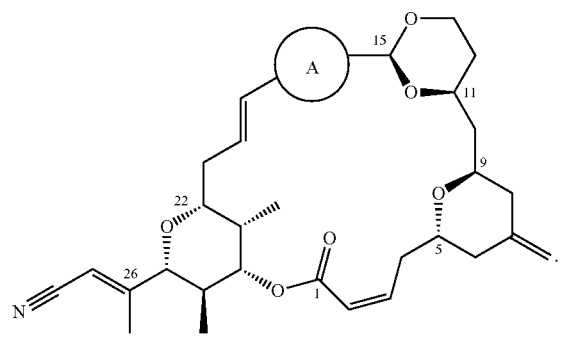

Also within the scope of the invention are pharmaceutical compositions comprising a compound the invention and at least one pharmaceutically acceptable carrier or diluent.

Within the scope of the invention are compounds of the following formula:

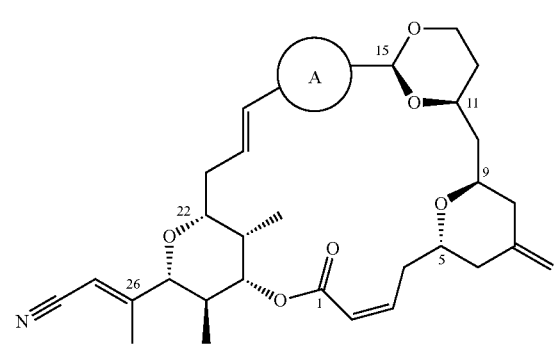

wherein ring A is aryl or a 5- or 6-membered heteroaryl; as well as the pharmaceutically acceptable salt forms thereof; wherein the stereochemistry at least one of positions C(5), C(9), C(11), C(15), C(22), C(23), C(24), C(25), and C(26) is as shown above.

Preferably, the stereochemistry at at least three of positions C(5), C(9), C(11), C(15), C(22), C(23), C(24), C(25), and C(26) is as shown below:

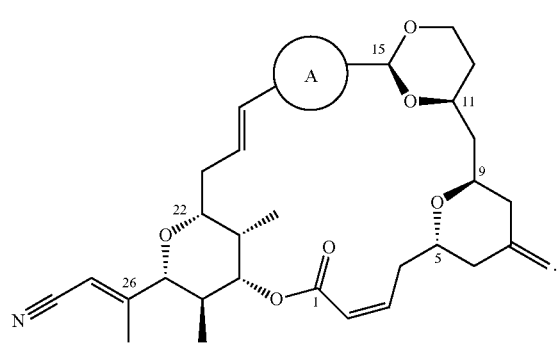

More preferably, the stereochemistry at at least six of positions C(5), C(9), C(11), C(15), C(22), C(23), C(24), C(25), and C(26) is as shown below:

Even more preferably, the stereochemistry at positions C(5), C(9), C(11), C(15), C(22), C(23), C(24), C(25), and C(26) is as shown below:

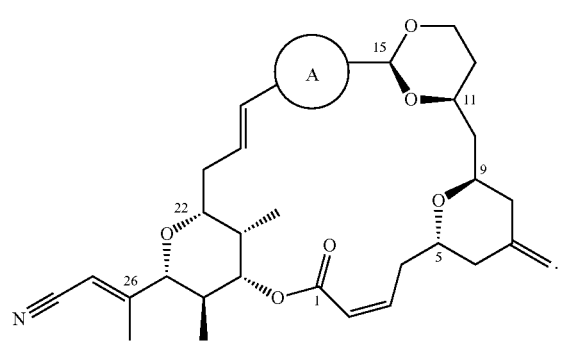

Also within the scope of the invention is the use of a compound of the invention for treating cancer in a patient by administering to the patient a therapeutically effective amount of a compound of the invention.

Preferred compounds for use in these methods are of the following formula:

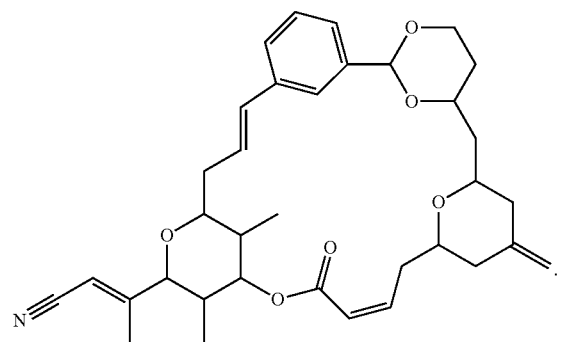 [SMILES: C=C1CC2C/C=C\C(=O)OC3C(C)C(C/C=C/c4cccc(c4)C4OCCC(CC(C1)O2)O4)OC(/C(C)=C/C#N)C3C]

Another preferred compound for use in these methods is:

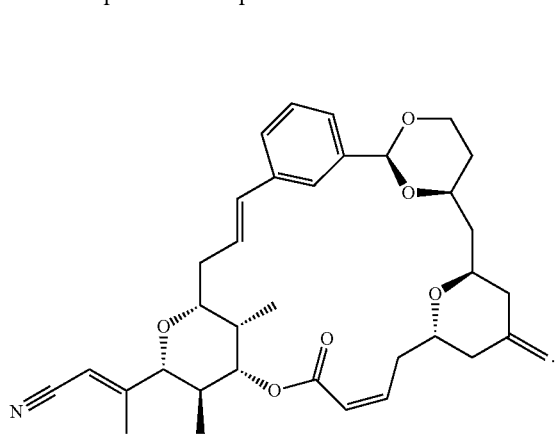

In preferred embodiments, the cancer is colon cancer or breast cancer.

Also within the scope of the invention is the use of a compound of the invention for treating a fungal infection in a patient by administering to the patent a therapeutically effective amount of a compound of the invention.

Preferred compounds for use in the invention include those of the following formula:

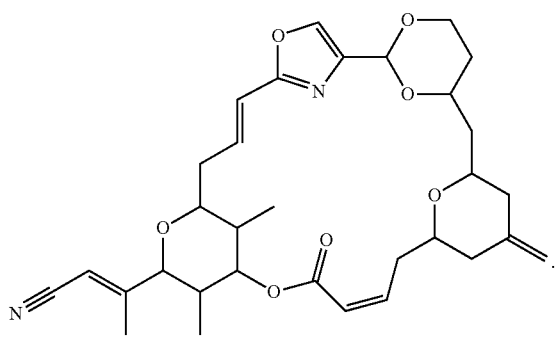 [SMILES: C=C1CC2C/C=C\C(=O)OC3C(C)C(C/C=C/c4nc(co4)C4OCCC(CC(C1)O2)O4)OC(/C(C)=C/C#N)C3C]

Another preferred compound for use in the invention is:

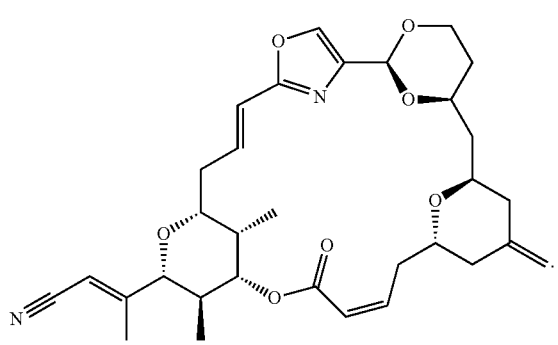

In preferred embodiments, the fungal infection comprises *Candida albicans*.

Also within the scope of the invention are compounds of the following formula:

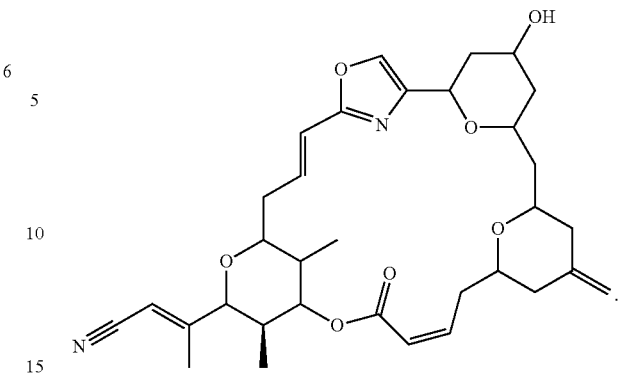

Preferably, the stereochemistry at at least one of positions C(5), C(9), C(11), C(13), C(15), C(22), C(23), C(24), C(25) and C(26) is as shown below:

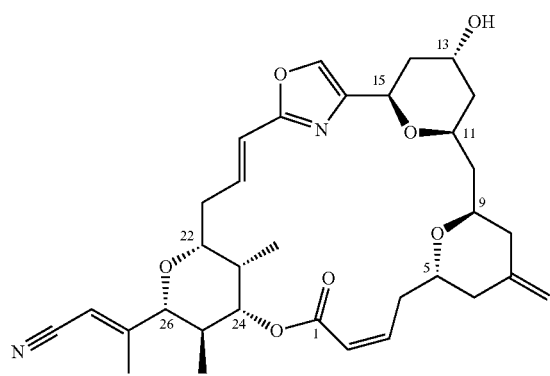 [SMILES: C=C1C[C@@H]2C[C@@H]3C[C@@H](O)C[C@@H](O3)c3coc(n3)/C=C/C[C@H]3O[C@@H](/C(C)=C/C#N)[C@H](C)[C@@H](OC(=O)/C=C\C[C@@H](C1)O2)[C@H]3C]

More preferably, the stereochemistry at at least three of positions C(5), C(9), C(11), C(13), C(15), C(22), C(23), C(24), C(25) and C(26) is as shown below:

Even more preferably, the stereochemistry at at least six of positions C(5), C(9), C(11), C(13), C(15), C(22), C(23), C(24), C(25) and C(26) is as shown below:

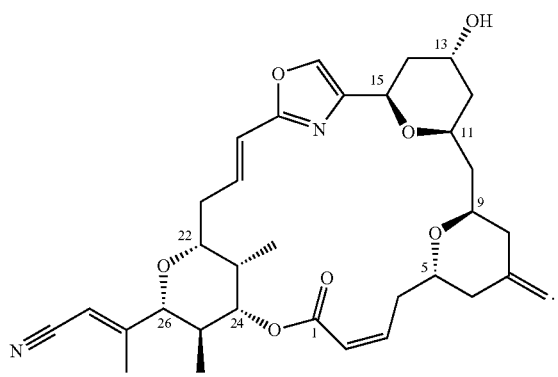 [SMILES: C=C1C[C@@H]2C[C@@H]3C[C@@H](O)C[C@@H](O3)c3coc(n3)/C=C/C[C@H]3O[C@@H](/C(C)=C/C#N)[C@H](C)[C@@H](OC(=O)/C=C\C[C@@H](C1)O2)[C@H]3C]

More preferred are compounds where the stereochemistry at positions C(5), C(9), C(11), C(13), C(15), C(22), C(23), C(24), C(25) and C(26) is as shown below:

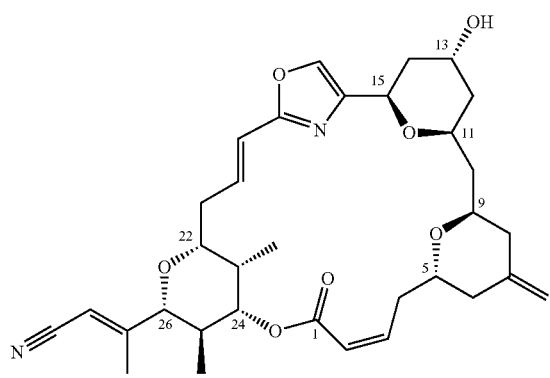 [SMILES: C=C1C[C@@H]2C[C@@H]3C[C@@H](O)C[C@@H](O3)c3coc(n3)/C=C/C[C@H]3O[C@@H](/C(C)=C/C#N)[C@H](C)[C@@H](OC(=O)/C=C\C[C@@H](C1)O2)[C@H]3C]

Pharmaceutical compositions comprising a compound the invention and at least one pharmaceutically acceptable carrier or diluent are also within the scope of the invention.

The following examples are set forth to further illustrate the invention and are not intended to limit the scope of the invention.

Experimental Section

Materials and Methods

All solvents used were reagent grade. Dichloromethane, tetrahydrofuran (THF), and toluene were filtered through an activated alumina and copper purification system (Pure Solv. PS-400) prior to use. All other reagents were purchased from Aldrich or Acros and used as received unless otherwise mentioned. Reactions, carried out in flame-dried or oven-dried glassware, were magnetically stirred under an argon atmosphere and monitored by thin layer chromatography (TLC) with 0.25 mm E. Merck pre-coated silica gel plates. Silica gel chromatography was performed with silica gel 60 (particle size 0.040-0.062 mm) supplied by Silicycle and Sorbent Technologies. Yields refer to chromatographically and spectroscopically pure compounds, unless otherwise stated. Infrared spectra were recorded on a Jasco Model FT/IR-480 Plus spectrometer. NMR spectra were recorded on a Bruker AMX-500 spectrometer. Chemical shifts are reported relative to chloroform ($\delta$ 7.26 and 77.23 for $^{1}$H and $^{13}$C NMR, respectively), or benzene ($\delta$ 7.16 and 128.39 for $^{1}$H and $^{13}$C NMR, respectively). Optical rotations were measured on a Perkin-Elmer model 241 polarimeter. High resolution mass spectra were measured at the University of Pennsylvania Mass Spectrometry Service Center.

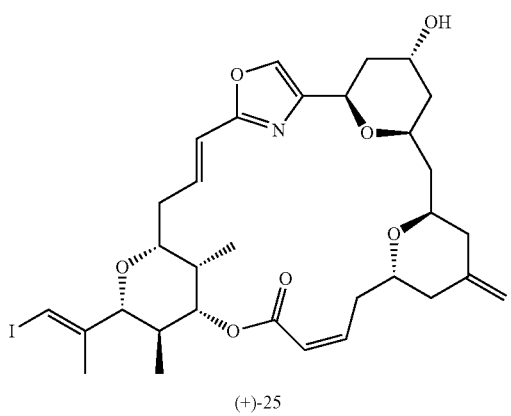 [SMILES: C=C1C[C@@H]2C[C@@H]3C[C@@H](O)C[C@@H](O3)c3coc(n3)/C=C/C[C@H]3O[C@@H](/C(C)=C/I)[C@H](C)[C@@H](OC(=O)/C=C\C[C@@H](C1)O2)[C@H]3C]

(+)-25

Preparation of Alcohol (+)-25

Tetrabutylammonium fluoride (0.3 mL, 1.0 M in THF) was added dropwise to a solution of vinyl iodide (+)-4 (8.0 mg, 0.01 mmol) in THF (3 mL) at 0° C. The resultant solution was stirred at 0° C. for 12 h. Brine (3 mL) was added and the mixture was extracted with ethyl acetate (3×3 mL). The combined organic layers were dried over sodium sulfate and concentrated to dryness. Silica gel chromatography (25% EtOAc/hexanes) afforded alcohol (+)-25 (6.4 mg, 94%): $[\alpha]_D^{20}$ +37.50 (c 0.7, CHCl$_3$); IR (thin film, CH$_2$Cl$_2$) 3449 (br, w), 3070 (w), 2924 (s), 1719 (s), 1187 (m), 1090 (m) cm$^{-1}$; $^{1}$H NMR (500 MHz, CDCl$_3$) $\delta$ 7.42 (s, 1H), 6.66 (ddd, 1H, J=16.2, 9.9, 6.5 Hz), 6.31 (s, 1H), 6.28 (d, 1H, J=15.9 Hz), 5.95-5.89 (m, 2H), 4.98 (s, 1H), 4.73 (dd, 1H, J=10.5, 3.2 Hz), 4.60 (s, 1H), 4.47 (dd, 1H, J=11.2, 4.4 Hz), 4.39 (s, 1H), 4.19-4.15 (m, 1H), 4.07-4.03 (m, 1H), 3.99-3.92 (m, 1H), 3.63 (d, 1H, J=10.2 Hz), 3.52-3.43 (m, 2H), 2.70 (d, 1H, J=12.3 Hz), 2.53-2.47 (m, 1H), 2.43-2.38 (m, 2H), 2.33-2.25 (m, 2H), 2.04 (d, 1H, J=12.8 Hz), 2.01-1.93 (m, 3H), 1.92-1.84 (m, 2H), 1.86 (s, 3H), 1.71 (d, 1H, J=4.0 Hz), 1.62-1.54 (m, 2H) 1.45-1.40 (m, 1H), 0.93 (d, 3H, J=6.9 Hz), 0.72 (d, 3H, J=6.4 Hz); $^{13}$C NMR (125 MHz, CDCl$_3$) $\delta$ 165.8, 161.5, 145.9, 144.8, 142.3, 142.0, 134.0, 133.9, 121.1, 119.6, 110.3, 88.0, 82.0, 79.2, 78.4, 73.7, 69.3, 68.4, 67.1, 64.6, 41.5, 39.2, 37.2, 35.2, 34.5, 32.7, 32.0, 30.7, 19.4, 13.3, 6.2; high resolution mass spectrum (ES+) m/z 702.1895 [M+NO'; calcd for C$_{32}$H$_{42}$INNaO$_7$: 702.1904].

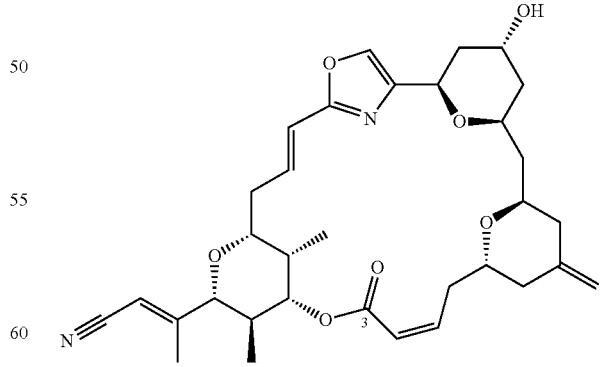

Preparation of Hemi-Phorboxazole A [(+)-3]

To a solution of vinyl iodide (+)-25 (4.0 mg, 0.0059 mmol) in anhydrous benzene (0.3 mL) was added copper iodide (0.2 mg, 0.0010 mmol), tetrakis(triphenylphosphine)palladium (0) (2.0 mg, 0.0018 mmol) and tributyltin cyanide (2.1 mg, 0.0071 mmol) sequentially. The mixture was heated at reflux in a sealed tube for 2 h. The solvent was removed in vacuo and the crude oil was purified directly by flash chromatography (25% EtOAc/hexanes) to provide hemi-phorboxazole (3.0 mg, 90%): $[\alpha]_D^{20}$+42.30 (c 0.2, CHCl$_3$); IR (thin film, CH$_2$Cl$_2$) 3436 (br, w), 3070 (w), 2930 (s), 2220 (m), 1718 (s), 1187 (s), 1093 (s) cm$^{-1}$; $^1$H NMR (500 MHz, CDCl$_3$) δ 7.42 (s, 1H), 6.65 (ddd, 1H, J=16.0, 9.7, 6.3 Hz), 6.29 (d, 1H, J=16.0 Hz), 5.98-5.89 (m, 2H), 5.32 (s, 1H), 4.97 (s, 1H), 4.74 (dd, 1H, J=10.9, 3.0 Hz), 4.60 (s, 1H), 4.48 (dd, 1H, J=11.2, 4.4 Hz), 4.42-4.38 (m, 1H), 4.19-4.14 (m, 1H), 4.08-4.03 (m, 1H), 4.01-3.94 (m, 1H), 3.56 (d, 1H, J=10.2 Hz), 3.53-3.44 (m, 2H), 2.70 (d, 1H, J=12.4 Hz), 2.53-2.47 (m, 1H), 2.44-2.37 (m, 2H), 2.36-2.32 (m, 2H), 2.10 (s, 3H), 2.07 (d, 1H, J=13.1 Hz), 2.01-1.93 (m, 3H), 1.92-1.88 (m, 2H), 1.71 (d, 1H, J=13.7 Hz), 1.64-1.54 (m, 2H), 1.43 (ddd, 1H, J=13.3, 10.0, 3.1 Hz), 0.93 (d, 3H, J=6.9 Hz), 0.76 (d, 3H, J=6.4 Hz); $^{13}$C NMR (125 MHz, CDCl$_3$) δ 165.6, 161.3, 161.0, 145.0, 142.3, 142.0, 133.9, 133.5, 120.9, 120.0, 116.3, 110.1, 99.1, 86.3, 78.7, 78.6, 73.6, 69.3, 68.8, 67.1, 64.6, 41.4, 39.2, 39.1, 37.1, 35.1, 34.3, 32.6, 32.0, 30.7, 16.6, 13.1, 6.0; high resolution mass spectrum (ES+) m/z 601.2899 [(M+Na)$^+$; calcd for C$_{33}$H$_{42}$N$_2$NaO$_7$: 601.2992].

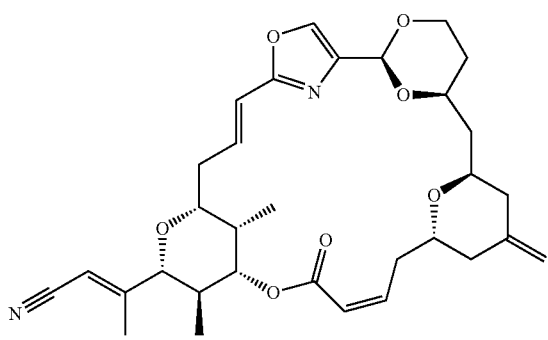

Preparation of Hemi-Phorboxazole Analogue (+)-5

To a solution of vinyl iodide (+)-15 (4.6 mg, 0.0069 mmol) in anhydrous benzene (0.4 mL) was added copper iodide (0.3 mg, 0.00158 mmol), tetrakis(triphenylphosphine)palladium (0) (2.4 mg, 0.0021 mmol) and tributyltin cyanide (2.6 mg, 0.0083 mmol) sequentially. The mixture was heated at reflux in a sealed tube for 2 h. The solvent was removed in vacuo and the crude oil was purified directly by flash chromatography (25% to 33% EtOAc/hexanes) to provide (+)-5 (3.0 mg, 90%): $[\alpha]_D^{20}$+43.90 (c 0.2, CHCl$_3$); IR (thin film, CH$_2$Cl$_2$) 2934 (s), 2857 (s), 2221 (m), 1717 (s), 1639 (m), 1234 (m), 1192 (s) cm$^{-1}$; $^1$H NMR (500 MHz, CDCl$_3$) δ 7.60 (s, 1H), 6.67 (ddd, 1H, J=16.2, 10.5, 6.1 Hz), 6.29 (d, 1H, J=15.9 Hz), 5.99-5.90 (m, 2H), 5.47 (s, 1H), 5.32 (s, 1H), 4.93 (s, 1H), 4.62 (s, 1H), 4.47 (dd, 1H, J=11.2, 4.3 Hz), 4.24 (dd, 1H, J=11.5, 4.6 Hz), 4.20-4.16 (m, 1H), 4.03-3.98 (m, 1H), 3.96-3.89 (m, 2H), 3.56 (d, 1H, J=10.3 Hz), 3.51 (dd, 1H, J=10.7, 5.2 Hz), 3.40 (ddd, 1H, J=14.0, 12.3, 9.5 Hz), 2.61 (d, 1H, J=12.3 Hz), 2.53-2.47 (m, 1H), 2.45-2.34 (m, 4H), 2.10 (s, 3H), 2.05 (d, 1H, J=11.4 Hz), 2.02-1.81 (m, 5H), 1.52 (d, 1H, J=13.2 Hz), 0.93 (d, 3H, J=6.9 Hz), 0.76 (d, 3H, J=6.5 Hz); $^{13}$C NMR (125 MHz, CDCl$_3$) δ 165.7, 161.3, 161.0, 145.0, 141.7, 139.9, 135.0, 133.9, 120.9, 119.5, 116.3, 110.3, 99.2, 97.2, 86.4, 78.9, 78.7, 73.5, 73.5, 68.5, 67.2, 41.4, 39.3, 37.1, 34.2, 32.6, 32.1, 30.6, 16.6, 13.1, 6.0; high resolution mass spectrum (ES+) m/z 587.2733 [(M+Na)$^+$; calcd for C$_{32}$H$_4$ON$_2$NaO$_7$: 587.2722].

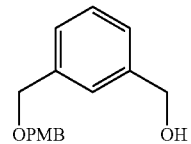

Preparation of PMB-Ether 26

Sodium hydride (460.2 mg, 11.50 mmol) was added to a solution of 1,3-benzenedimethanol (1.58 g, 11.44 mmol) in DMF (15 mL) at 0° C. After 10 min, the ice bath was removed and stirring continued at rt for 1 h. The reaction was then re-cooled to 0° C. and dropwise addition of 4-methoxybenzyl bromide (1.65 mL, 11.44 mmol) was followed by addition of tetrabutylammonium iodide (421.5 mg, 1.14 mmol). The resultant mixture was warmed to rt and stirring continued for 16 h. Hydrochloric acid (5 mL, 1 M) was added and the reaction mixture diluted with ethyl acetate (80 mL). The organic layer was separated, washed with brine (×3), dried over sodium sulfate and concentrated to dryness. Silica gel chromatography (20% to 50% EtOAc/hexanes) afforded 26 as colorless oil (1.22 g, 41%), (the di-protected compound was also isolated in 23% yield): IR (neat) 3389 (br, m), 2934 (m), 2860 (m), 2836 (m), 1612 (m), 1515 (s) cm$^{-1}$; $^1$H NMR (CDCl$_3$, 500 MHz) δ 7.35-7.26 (m, 6H), 6.91 (d, 2H, J=8.5 Hz), 4.62 (s, 2H), 4.53 (s, 2H), 4.51 (s, 2H), 3.82 (s, 3H); $^{13}$C NMR (CDCl$_3$, 125 MHz) δ 159.3, 141.3, 138.6, 130.3, 129.6, 128.6, 127.0, 126.4, 126.3, 113.9, 72.0, 71.8, 65.0, 55.3; high resolution mass spectrum (ES$^+$) m/z 281.1146 [(M+Na)$^+$; calcd for C$_{16}$H$_{18}$O$_3$Na: 281.1154].

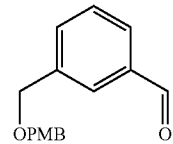

Preparation of Aldehyde 16

Manganese dioxide (2.57 g, 29.56 mmol) was added to a solution of alcohol 26 (743.9 mg, 2.88 mmol) in dichloromethane (50 mL). The reaction was stirred at rt for 16 h. Flash chromatography on silica gel (20% to 50% EtOAc/hexanes) afforded 16 as colorless oil (695.7 mg, 94%): IR (neat) 2930 (m), 2851 (m), 2837 (m), 1701 (m), 1607 (m), 1513 (m) cm$^{-1}$; $^1$H NMR (CDCl$_3$, 500 MHz) δ 10.0 (s, 1H), 7.87 (s, 1H), 7.81 (d, 1H, J=7.5 Hz), 7.63 (d, 1H, J=7.5 Hz), 7.52 (t, 1H, J=7.5 Hz), 7.30 (d, 2H, J=8.4 Hz), 6.90 (d, 2H, J=8.4 Hz), 4.59 (s, 2H), 4.54 (s, 2H), 3.81 (s, 3H); $^{13}$C NMR (CDCl$_3$, 125 MHz) δ 192.5, 159.6, 139.9, 136.7, 133.8, 130.1, 129.7, 129.3, 129.1, 129.0, 114.1, 72.5, 71.2, 55.5; high resolution mass spectrum (ES$^+$) m/z 279.0991 [(M+Na)$^+$; calcd for C$_{16}$H$_{16}$O$_3$Na: 279.0997].

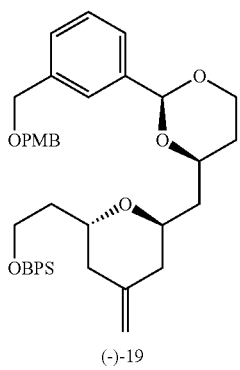

(−)-19

Preparation of Acetal (−)-19

10-Camphorsulfonic acid (4.4 mg, 17.6 μmol) and sodium sulfate (238.5 mg, 1.89 mmol) were added to a solution of diol (−)-18 (49.8 mg, 0.11 mmol) and aldehyde 16 (38.0 mg, 0.15 mmol) in toluene (4 mL). The reaction was heated at 90° C. for 24 h. The reaction mixture was cooled to rt, diluted with ethyl acetate and washed with phosphate buffer pH 7. The organic layer was dried over sodium sulfate and concentrated to dryness. Silica gel chromatography (5% to 10% EtOAc/hexanes) afforded (−)-19 as colorless oil (73.3 mg, 94%): $[\alpha]_D^{29}$ −22.2 (c 0.22, CHCl$_3$); IR (neat) 2935 (m), 2856 (m), 1513 (m), 1248 (m), 1109 (s) cm$^{-1}$; $^1$H NMR (CDCl$_3$, 500 MHz) δ 7.71-7.66 (m, 4H), 7.44-7.34 (m, 10H), 7.30-7.28 (m, 2H), 6.90-6.88 (m, 2H), 5.40 (s, 1H), 4.77 (s, 2H), 4.53 (s, 2H), 4.47 (s, 2H), 4.18 (dd, 1H, J=11.2, 4.9 Hz), 4.06-4.04 (m, 1H), 3.96-3.89 (m, 2H), 3.81 (s, 3H), 3.78-3.76 (m, 2H), 3.72-3.69 (m, 1H), 2.36 (dt, 2H, J=13.2, 4.8 Hz), 2.13 (ddd, 1H, J=13.9, 9.2, 5.7), 2.03 (ddd, 2H, J=20.5, 13.2, 6.3 Hz), 1.89-1.84 (m, 1H), 1.78-1.66 (m, 2H), 1.56-1.51 (m, 2H), 1.06 (s, 9H); $^{13}$C NMR (CDCl$_3$, 125 MHz) δ: 159.4, 142.1, 139.1, 138.6, 135.7, 134.0, 130.6, 129.8, 129.6, 128.5, 128.2, 127.9, 125.6, 125.5, 114.0, 110.7, 101.3, 74.2, 71.9, 71.8, 69.1, 68.1, 67.1, 60.8, 55.5, 40.0, 39.8, 39.4, 36.6, 31.1, 27.1, 19.4; high resolution mass spectrum (ES$^+$) m/z 729.3607 [(M+Na)$^+$; calcd for C$_{44}$H$_{54}$O$_6$SiNa: 729.3587].

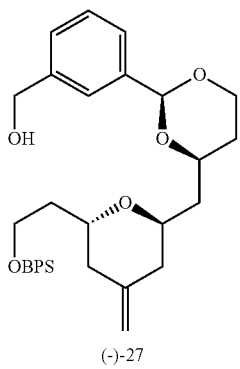

(−)-27

Preparation of Alcohol (−)-27

A solution of PMB-ether (−)-19 (278.3 mg, 0.39 mmol) in dichloromethane (39 mL) and water (2.5 mL) was cooled to 0° C. DDQ (133.5 mg, 0.59 mmol) was added in one portion. After 10 min the ice bath was removed and stirring continued at rt for 16 h. The reaction was quenched by the addition of saturated sodium bicarbonate solution (15 mL) and the organic layer was separated. The aqueous layer was extracted with dichloromethane (30 mL); the combined organic layers were dried over sodium sulfate and concentrated to dryness. Silica gel chromatography (25% to 50% EtOAc/hexanes) afforded (−)-27 as colorless oil (222.8 mg, 97%): $[\alpha]_D^{29}$ −18.9 (c 0.47, CHCl$_3$); IR (neat) 3421 (br, w), 2930 (m), 2857 (m), 1109 (s) cm$^{-1}$; $^1$H NMR (CDCl$_3$, 500 MHz) δ 7.70-7.65 (m, 4H), 7.46 (s, 1H), 7.42-7.32 (m, 9H), 5.39 (s, 1H), 4.76 (s, 2H), 4.68 (s, 2H), 4.17 (dd, 1H, J=11.3, 4.6 Hz), 4.05-4.03 (m, 1H), 3.94-3.90 (m, 2H), 3.80-3.75 (m, 2H), 3.70-3.66 (m, 1H), 2.35 (ddd, 2H, J=13.1, 8.0, 4.7 Hz), 2.12 (ddd, 1H, J=14.1, 9.1, 5.5 Hz), 2.05-1.95 (m, 2H), 1.86-1.83 (m, 1H), 1.78-1.63 (m, 2H), 1.60 (bs, 1H), 1.57-1.51 (m, 2H), 1.05 (s, 9H); $^{13}$C NMR (CDCl$_3$, 125 MHz) δ 142.1, 141.1, 139.3, 135.8, 134.1, 129.9, 128.7, 127.9, 127.9, 127.5, 125.7, 124.8, 110.7, 101.2, 74.3, 69.1, 68.2, 67.2, 65.6, 60.9, 40.0, 39.9, 39.4, 36.7, 31.1, 27.1, 19.4; high resolution mass spectrum (ES$^+$) m/z 609.2998 [(M+Na)$^+$; calcd for C$_{36}$H$_{46}$O$_5$SiNa: 609.3012].

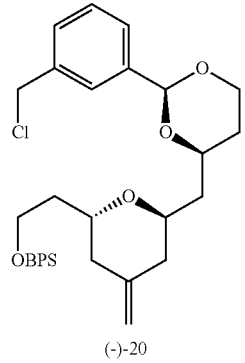

(−)-20

Preparation of Chloride (−)-20

Carbon tetrachloride (3 mL) and triphenylphosphine (907.1 mg, 3.46 mmol) were added to a solution of alcohol (−)-27 (202.2 mg, 0.34 mmol) in dichloromethane (15 mL) at rt. Stirring continued at rt for 1.5 h. The reaction mixture was poured onto saturated sodium bicarbonate solution (10 mL) and extracted with dichloromethane (2×20 mL). The combined organic layers were dried over sodium sulfate and concentrated to dryness. Silica gel chromatography (5% EtOAc/hexanes) afforded (−)-20 as colorless oil (186.9 mg, 91%): $[\alpha]_D^{29}$ −23.2 (c 0.18, CHCl$_3$); IR (neat) 2930 (m), 2857 (m), 1110 (s) cm$^{-1}$; $^1$H NMR (CDCl$_3$, 500 MHz) δ 7.69-7.65 (m, 4H), 7.46 (s, 1H), 7.42-7.34 (m, 9H), 5.37 (s, 1H), 4.76 (s, 2H), 4.57 (s, 2H), 4.17 (dd, 1H, J=11.4, 4.3 Hz), 4.07-4.01 (m, 1H), 3.96-3.87 (m, 2H), 3.80-3.75 (m, 2H), 3.72-3.67 (m, 1H), 2.38-2.33 (m, 2H), 2.13-2.09 (m, 1H), 2.05-1.98 (m, 2H), 1.88-1.84 (m, 1H), 1.75-1.65 (m, 2H), 1.57-1.51 (m, 2H), 1.05 (s, 9H); $^{13}$C NMR (CDCl$_3$, 125 MHz) δ 142.1, 139.5, 137.6, 135.8, 134.0, 129.9, 129.0, 128.8, 127.9, 127.8, 126.5, 126.4, 110.7, 100.9, 74.3, 69.1, 68.2, 67.1, 60.8, 46.3, 40.0, 39.8, 39.4, 36.7, 31.1, 27.1, 19.4; high resolution mass spectrum (ES$^+$) m/z 627.2657 [(M+Na)$^+$; calcd for C$_{36}$H$_{45}$O$_4$SiClNa: 627.2673].

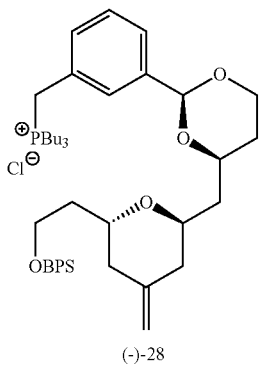

(−)-28

Preparation of Wittig Salt (−)-28

Tri-n-butylphosphine (0.07 mL, 0.28 mmol) was added to a solution of chloride (−)-20 (155.3 mg, 0.26 mmol) in DMF (7.5 mL). After stirring at rt for 16 h, additional tri-n-butylphosphine (0.12 mL, 0.49 mmol) was added. The reaction was stirred at rt for a further 48 h. The solvent was removed under reduced pressure. Silica gel chromatography (5% to 10% methanol/dichloromethane) afforded (−)-28 as colorless oil (205.9 mg, 98%): $[\alpha]_D^{28}$−28.0 (c 0.10, CHCl$_3$); IR (neat) 2952 (m), 2930 (m), 2871 (m), 2868 (m), 1110 (s) cm$^{-1}$; $^1$H NMR (CDCl$_3$, 500 MHz) δ 7.66-7.64 (m, 4H), 7.51-7.50 (m, 1H), 7.41-7.33 (m, 8H), 7.30 (s, 1H), 5.35 (s, 1H), 4.76 (s, 1H), 4.75 (d, 1H, J=4.1 Hz), 4.19 (quintet, 2H, J=15.4 Hz), 4.12 (dd, 1H, J=11.3, 4.7 Hz), 4.03-4.01 (m, 1H), 3.91-3.88 (m, 2H), 3.77-3.73 (m, 2H), 3.69-3.66 (m, 1H), 2.41-2.32 (m, 8H), 2.09-2.06 (m, 1H), 2.03-1.97 (m, 2H), 1.85-1.82 (m, 1H), 1.69-1.65 (m, 2H), 1.53-1.45 (m, 14H), 1.03 (s, 9H), 0.94-0.91 (m, 9H); $^{13}$C NMR (CDCl$_3$, 125 MHz) δ 142.0, 135.7, 134.0, 131.1, 129.8, 129.6, 128.5, 127.9, 127.8, 127.4, 126.5, 110.7, 100.4, 74.3, 69.1, 68.1, 67.1, 60.8, 39.9, 39.8, 39.4, 36.7, 31.1, 27.1, 24.2, 24.1, 24.0, 23.9, 19.4, 19.0, 18.6, 13.6; high resolution mass spectrum (ES$^+$) m/z 772.5005 [(M+H)$^+$—Cl; calcd for C$_{48}$H$_{73}$O$_4$Si: 772.5016].

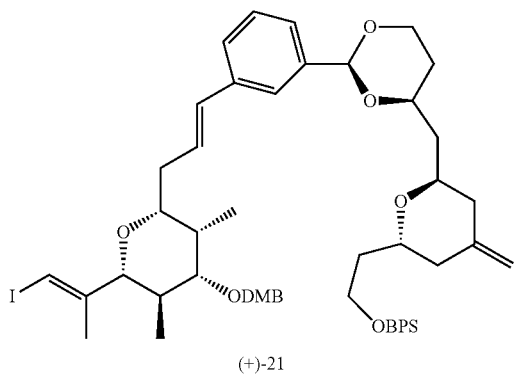

(+)-21

Preparation of Styrene (+)-21

Potassium tert-butoxide (0.18 mL, 1 M in THF) was added dropwise to a solution of Wittig salt (−)-28 (115.3 mg, 0.14 mmol) and aldehyde (+)-17 (70.9 mg, 0.15 mmol) in toluene (18 mL) at 0° C. Stirring continued at 0° C. for 4.5 h. The reaction was quenched by the addition of water (5 mL) and the organic layer separated. The aqueous layer was extracted with ethyl acetate (10 mL) and the combined organic layers were dried over sodium sulfate and concentrated to dryness. Silica gel chromatography (20% EtOAc/hexanes) afforded 21 as colorless oil (137.6 mg, 94%, E:Z=4/1). Separation of E/Z-isomers was not achieved at this stage and the product was carried forward as a mixture of isomers until after macrocyclization. An analytically pure sample of (+)-21 (E-isomer) was obtained by chromatography on silver nitrate impregnated silica gel (20% EtOAc/hexanes): $[\alpha]_D^{17}$+12.1 (c 0.28, CDCl$_3$); IR (neat): 2925 (m), 2854 (m), 1461 (m), 1108 (m) cm$^{-1}$; $^1$H NMR (CDCl$_3$, 500 MHz) δ 7.69-7.65 (m, 4H), 7.44 (s, 1H), 7.41-7.37 (m, 6H), 7.31-7.28 (m, 3H), 6.89-6.86 (m, 2H), 6.82-6.81 (m, 1H), 6.45 (d, 1H, J=15.9 Hz), 6.25 (s, 1H), 6.15 (ddd, 1H, J=15.9, 8.7, 8.0 Hz), 5.37 (s, 1H), 4.76 (s, 2H), 4.57 (d, 1H, J=11.2 Hz), 4.27 (d, 1H, J=11.2 Hz), 4.18 (dd, 1H, J=11.2, 4.9 Hz), 4.07-4.02 (m, 1H), 3.95-3.88 (m, 2H), 3.86 (s, 6H), 3.81-3.75 (m, 2H), 3.72-3.67 (m, 1H), 3.52 (d, 1H, J=10.2 Hz), 3.46 (t, 1H, J=7.2 Hz), 3.15 (dd, 1H, J=10.3, 4.6 Hz), 2.56-2.51 (m, 1H), 2.38-2.32 (m, 3H), 2.15-2.08 (m, 2H), 2.06-1.98 (m, 2H), 1.88-1.78 (m, 2H), 1.84 (s, 3H), 1.76-1.64 (m, 2H), 1.58-1.55 (m, 2H), 1.05 (s, 9H), 0.98 (d, 3H, J=7.0 Hz), 0.81 (d, 3H, J=6.5 Hz); $^{13}$C NMR (CDCl$_3$, 125 MHz) δ 149.2, 148.8, 146.7, 142.1, 139.2, 137.7, 135.8, 134.0, 132.3, 131.2, 129.9, 128.6, 127.9, 127.8, 126.7, 126.4, 125.2, 123.9, 120.4, 111.3, 111.2, 110.7, 101.4, 87.8, 83.3, 81.3, 78.5, 74.3, 70.1, 69.2, 68.2, 67.2, 60.9, 56.1, 56.0, 40.0, 39.9, 39.5, 36.6, 33.6, 33.5, 31.1, 27.1, 19.4, 19.4, 13.8, 5.9; high resolution mass spectrum (ES$^+$) m/z 1063.4034 [(M+Na)$^+$; calcd for C$_{57}$H$_{73}$O$_8$SiNa: 1063.4017].

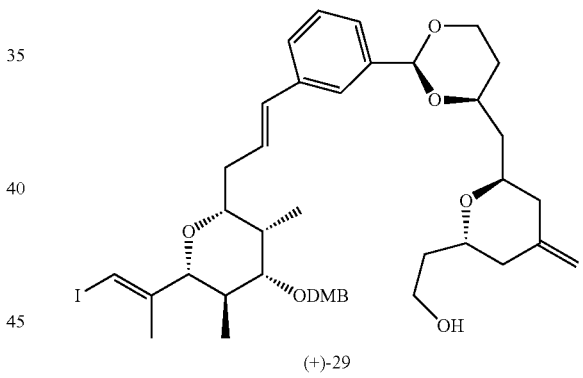

(+)-29

Preparation of Alcohol (+)-29

Tetrabutylammonium fluoride (0.11 mL, 1 M in THF) was added to a solution of tetracycle 21 (108.7 mg, 0.10 mmol) in THF (2.5 mL) at rt. Stirring continued at rt for 1.5 h. The reaction was quenched by dropwise addition of brine and diluted with ethyl acetate (5 mL). The organic layer was separated, dried over sodium sulfate and concentrated to dryness. Silica gel chromatography (20% to 80% EtOAc/hexanes) afforded 29 as colorless oil (75.7 mg, 95%). Complete separation of E/Z-isomers (from Wittig reaction) was not achieved at this stage, however an analytically pure sample of (+)-29 was obtained by chromatography on silver nitrate impregnated silica gel (50% EtOAc/hexanes): $[\alpha]_D^{29}$+23.5 (c 0.38, CDCl$_3$); IR (neat) 3414 (br, w), 2929 (m), 2851 (m), 1516 (m) cm$^{-1}$; $^1$H NMR (CDCl$_3$, 500 MHz) δ 7.49 (s, 1H), 7.34-7.30 (m, 3H), 6.90-6.86 (m, 2H), 6.83-6.81 (m, 1H), 6.46 (d, 1H, J=16.1 Hz), 6.25 (s, 1H), 6.20-6.14 (m, 1H), 5.51

(s, 1H), 4.80 (s, 1H), 4.76 (s, 1H), 4.58 (d, 1H, J=11.3 Hz), 4.30-4.27 (m, 1H), 4.28 (d, 1H, J=11.3 Hz), 4.18-4.14 (m, 1H), 4.01-3.94 (m, 3H), 3.86 (s, 6H), 3.75-3.71 (m, 2H), 3.53 (d, 1H, J=10.5 Hz), 3.46 (t, 1H, J=6.9 Hz), 3.15 (dd, 1H, J=10.5, 4.6 Hz), 2.56-2.51 (m, 1H), 2.47-2.44 (m, 1H), 2.38-2.28 (m, 3H), 2.23-2.13 (m, 2H), 2.09-2.01 (m, 2H), 1.88-1.80 (m, 3H), 1.84 (s, 3H), 1.65-1.59 (m, 3H), 0.98 (d, 3H, J=7.0 Hz), 0.81 (s, 3H, J=6.4 Hz); $^{13}$C NMR (CDCl$_3$, 125 MHz) δ 149.2, 148.8, 146.7, 141.5, 139.1, 137.7, 132.3, 131.2, 128.7, 126.8, 126.5, 125.3, 124.0, 120.4, 111.3, 111.1, 111.0, 101.6, 87.8, 83.3, 81.3, 78.5, 74.7, 71.6, 70.1, 69.5, 67.3, 61.3, 56.1, 56.0, 40.4, 39.1, 38.4, 36.7, 36.6, 33.6, 33.5, 31.4, 19.4, 13.8, 5.9; high resolution mass spectrum (ES$^+$) m/z 803.3016 [(M+H)$^+$; calcd for C$_{41}$H$_{56}$O$_8$I: 803.3020].

39.5, 39.3, 36.6, 33.6, 33.5, 31.2, 19.4, 13.8, 5.9; high resolution mass spectrum (ES$^+$) m/z 823.2714 [(M+Na)$^+$; calcd for C$_{41}$H$_{53}$O$_8$INa: 823.2683].

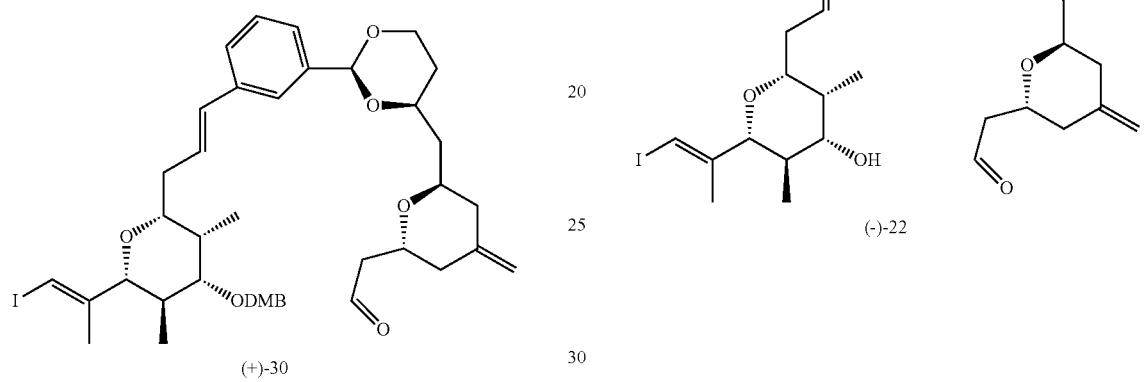

(+)-30

(−)-22

Preparation of Aldehyde (+)-30

Dess-Martin periodinane (84.4 mg, 0.20 mmol) and sodium bicarbonate (7.9 mg, 0.094 mmol) were added to a solution of alcohol 29 (75.7 mg, 0.094 mmol) in dichloromethane (35 mL) at 0° C. After 10 min the ice bath was removed and stirring continued at rt for 4 h. The reaction was quenched by the dropwise addition of saturated sodium bicarbonate solution (10 mL). The organic layer was separated; the aqueous layer further extracted with dichloromethane (25 mL), and the combined organic layers dried over sodium sulfate and concentrated to dryness. Silica gel chromatography (20% to 50% EtOAc/hexanes) afforded 30 as colorless oil (69.9 mg, 93%). Complete separation of E/Z-isomers (from Wittig reaction) was not achieved at this stage, however an analytically pure sample of (+)-30 was obtained by chromatography on silver nitrate impregnated silica gel (25% EtOAc/hexanes): [α]$_D^{18}$+5.5 (c 0.24, C$_6$D$_6$); IR (neat) 2927 (m), 2851 (m), 1724 (m), 1516 (m) cm$^{-1}$; $^1$H NMR (CDCl$_3$, 500 MHz) δ 9.75 (s, 1H), 7.48 (s, 1H), 7.34-7.27 (m, 3H), 6.91-6.87 (m, 2H), 6.83-6.81 (m, 1H), 6.46 (d, 1H, J=15.7 Hz), 6.25 (s, 1H), 6.17 (ddd, 1H, J=15.7, 8.4, 5.6 Hz), 5.51 (s, 1H), 4.82 (s, 2H), 4.57 (d, 1H, J=11.2 Hz), 4.45-4.40 (m, 1H), 4.30-4.27 (m, 1H), 4.28 (d, 1H, J=11.2 Hz), 4.03-3.94 (m, 3H), 3.86 (s, 6H), 3.53 (d, 1H, J=10.2 Hz), 3.46 (t, 1H, J=7.2 Hz), 3.16 (dd, 1H, J=10.5, 4.6 Hz), 2.72 (ddd, 1H, J=16.1, 8.5, 3.2 Hz), 2.56-2.46 (m, 2H), 2.44-2.32 (m, 3H), 2.17-2.11 (m, 2H), 2.09-2.03 (m, 2H), 1.84 (s, 3H), 1.83-1.79 (m, 2H), 1.63-1.57 (m, 2H), 0.98 (d, 3H, J=6.9 Hz), 0.81 (d, 3H, J=6.5 Hz); $^{13}$C NMR (CDCl$_3$, 125 MHz) δ 200.8, 149.2, 148.8, 146.7, 140.9, 139.2, 137.7, 132.3, 131.2, 128.7, 126.8, 126.5, 125.3, 123.9, 120.4, 111.7, 111.3, 111.2, 101.6, 87.8, 83.3, 81.3, 78.5, 74.4, 70.1, 69.0, 67.5, 67.3, 56.2, 56.0, 47.8, 39.6, Preparation of Hydroxy-Aldehyde (−)-22

DDQ (5.8 mg, 0.026 mmol) was added to a solution of DMB-ether 30 (20.6 mg, 0.026 mmol) in phosphate buffer pH 7 (0.19 mL) and toluene (3.71 mL) at 0° C. After 10 min, the reaction was allowed to warm to rt and stirring continued for 18 h. The reaction mixture was diluted with buffer solution (pH 7) and extracted with ethyl acetate. The organic layer was separated, dried over sodium sulfate and concentrated to dryness. Silica gel chromatography (20% to 50% EtOAc/hexanes) afforded 22 as colorless oil (11.2 mg, 66%). Starting material 30 was also recovered in 12% yield. Complete separation of E/Z-isomers (from Wittig reaction) was not achieved at this stage, however an analytically pure sample of (−)-22 was obtained by chromatography on silver nitrate impregnated silica gel (25% EtOAc/hexanes): [α]$_D^{18}$−5.1 (c 0.24, CDCl$_3$); IR (neat) 3405 (br, w), 2924 (m), 1722 (m), 1104 (s) cm$^{-1}$; $^1$H NMR (CDCl$_3$, 500 MHz) δ 9.76 (s, 1H), 7.45 (s, 1H), 7.30-7.27 (m, 3H), 6.44 (d, 1H, J=15.8 Hz), 6.26 (s, 1H), 6.14 (ddd, 1H, J=15.8, 8.3, 6.9 Hz), 5.50 (s, 1H), 4.82 (s, 2H), 4.45-4.39 (m, 1H), 4.29-4.26 (m, 1H), 4.04-3.94 (m, 3H), 3.54-3.49 (m, 2H), 3.46-3.43 (m, 1H), 2.72 (ddd, 1H, J=16.2, 8.5, 3.0 Hz), 2.53-2.47 (m, 2H), 2.44-2.39 (m, 2H), 2.36-2.30 (m, 1H), 2.16-1.96 (m, 4H), 1.85 (s, 3H), 1.83-1.80 (m, 2H), 1.62-1.57 (m, 2H), 0.98 (d, 3H, J=6.9 Hz), 0.82 (d, 3H, J=6.4 Hz) [OH not observed]; $^{13}$C NMR (C$_6$D$_6$, 125 MHz) δ 199.7, 147.4, 141.8, 140.6, 138.2, 132.9, 128.9, 127.1, 126.9, 126.1, 124.8, 111.4, 102.1, 87.9, 81.0, 79.0, 76.7, 74.7, 69.1, 67.6, 67.4, 47.9, 39.9, 39.8, 38.4, 36.9, 35.1, 32.6, 31.6, 19.8, 13.6, 6.0; high resolution mass spectrum (ES$^+$) m/z 673.2007 [(M+Na)$^+$; calcd for C$_{32}$H$_{43}$O$_6$INa: 673.2002].

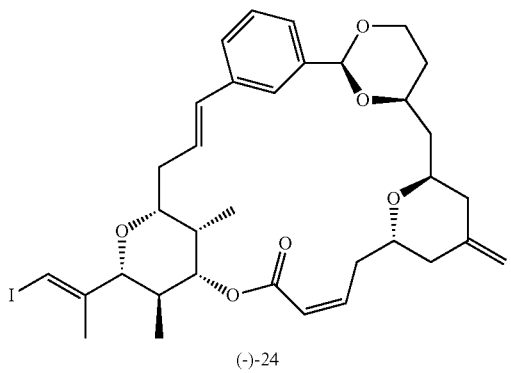 [SMILES: C=C1C[C@@H]2C[C@@H]3CCO[C@@H](O3)c3cccc(c3)/C=C/C[C@H]3O[C@@H](/C(C)=C/I)[C@H](C)[C@@H](OC(=O)/C=C\C[C@@H](C1)O2)[C@H]3C ; "(-)-24"]

(−)-24

Preparation of Vinyl Iodide (−)-24

A solution of hydroxy-aldehyde 22 (13.4 mg, 0.02 mmol) and 2-[bis-(2,2,2-trifluoroethoxy)phosphoryl]acetic acid (32.3 mg, 0.11 mmol) in dichloromethane (4.1 mL) was stirred at rt for 20 min. 1-(3-Dimethylaminopropyl)-3-ethyl-carbodiimide methiodide (30.1 mg, 0.10 mmol) and 1-hydroxybenzotriazole (0.6 mg, 4.44 μmmol) were added and stirring continued at rt for 5 h. The reaction mixture was filtered directly through a short plug of silica (50% EtOAc/hexanes) and concentrated to provide the phosphonate ester, which was used without further purification.

A solution of potassium carbonate (37.3 mg, 0.27 mmol) and 18-crown-6 (300.4 mg, 1.14 mmol) in toluene (18 mL) was stirred at rt for 3 h. To this solution was added dropwise a solution of the phosphonate ester (from above) in toluene (16 mL) and stirring continued at rt for 14 h. The reaction was quenched with brine (10 mL), the organic layer was separated and the aqueous layer was extracted with ethyl acetate (20 mL). The combined organic layers were dried over sodium sulfate and concentrated to dryness. Silica gel chromatography (20% EtOAc/hexanes) afforded (−)-24 as colorless oil (6.0 mg, 44%, Z-isomer), (the E-macrolide was also isolated in 15% yield): $[\alpha]_D^{29}$ −5.2 (c 0.17, CDCl$_3$); IR (neat) 2920 (m), 2850 (m), 1719 (m) cm$^{-1}$; $^1$H NMR (C$_6$D$_6$, 500 MHz) δ 7.71 (s, 1H), 7.64 (d, 1H, J=7.6 Hz), 7.24-7.04 (m, 2H), 6.41 (d, 1H, J=15.6 Hz), 6.02 (s, 1H), 5.92 (dt, 1H, J=15.6, 7.6 Hz), 5.86 (d, 1H, J=10.4 Hz), 5.61 (dt, 1H, J=10.4, 4.6 Hz), 5.31 (s, 1H), 4.82 (s, 1H), 4.74 (s, 1H), 4.66 (dd, 1H, J=11.0, 4.5 Hz), 4.22-4.18 (m, 1H), 3.98-3.93 (m, 2H), 3.66-3.59 (m, 2H), 3.53-3.44 (m, 2H), 3.13 (d, 1H, J=10.1 Hz), 3.13-3.29 (m, 1H), 2.53-2.51 (m, 1H), 2.46-2.41 (m, 3H), 2.27-2.24 (m, 1H), 1.97-1.86 (m, 3H), 1.83 (d, 3H, J=1.0 Hz), 1.65-1.55 (m, 3H), 0.98 (d, 3H, J=6.8 Hz), 0.79-0.77 (m, 1H), 0.64 (d, 3H, J=6.5 Hz); $^{13}$C NMR (C$_6$D$_6$, 125 MHz, cryogenic probe) δ 165.8, 146.8, 144.9, 142.9, 140.4, 138.4, 134.0, 130.5, 127.8, 125.7, 125.5, 124.1, 122.2, 110.6, 101.1, 88.0, 81.7, 79.5, 78.2, 74.4, 73.0, 69.0, 67.2, 41.5, 40.3, 38.2, 35.5, 33.6, 32.7, 32.0, 31.9, 19.6, 14.7, 13.5; high resolution mass spectrum (ES$^+$) m/z 697.1984 [(M+Na)$^+$; calcd for C$_{34}$H$_{43}$IO$_6$Na: 697.2002].

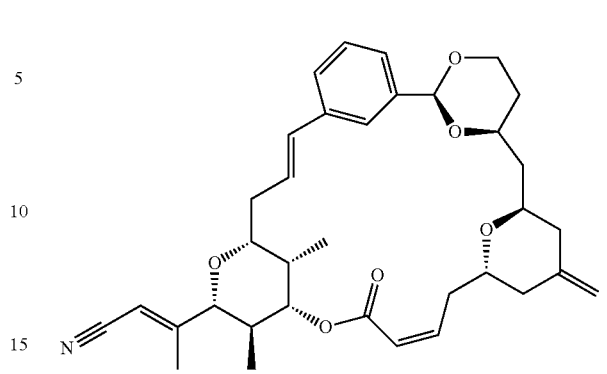

6

Preparation of Hemi-Phorboxazole Analogue 6

Vinyl iodide (−)-24 (3.8 mg, 5.63 μmmol), copper iodide (0.6 mg, 3.15 μmmol), tetrakis(triphenylphosphine)palladium(0) (1.8 mg, 1.56 mmol) and tributyltin cyanide (2.1 mg, 6.64 μmmol) were placed in a sealed tube and anhydrous benzene (0.4 mL) added. The reaction was heated at 80° C. for 3.5 h. After cooling to rt, silica gel chromatography (20% to 50% EtOAc/hexanes) afforded (−)-6 as colorless oil (3.0 mg, 93%): $[\alpha]_D^{30}$ −4.1 (c 0.30, C$_6$D$_6$); IR (neat) 2958 (m), 2923 (m), 2850 (m), 2219 (w), 1716 (m) cm$^{-1}$; $^1$H NMR (C$_6$D$_6$, 500 MHz) δ 7.73 (s, 1H), 7.63 (d, 1H, J=7.3 Hz), 7.19-7.09 (m, 2H), 6.42 (d, 1H, J=15.6 Hz), 5.90 (dt, 1H, J=15.6, 7.7 Hz), 5.85 (d, 1H, J=10.6 Hz), 5.64 (dt, 1H, J=10.6, 4.7 Hz), 5.32 (s, 1H), 4.81 (s, 1H), 4.72 (s, 1H), 4.67 (s, 1H), 4.58 (dd, 1H, J=11.1, 4.3 Hz), 4.23-4.17 (m, 1H), 3.97-3.93 (m, 2H), 3.64-3.58 (m, 2H), 3.52-3.45 (m, 2H), 3.21 (ddd, 1H, J=10.3, 5.3, 1.8 Hz), 3.00 (d, 1H, J=10.4 Hz), 2.49-2.35 (m, 5H), 2.26-2.22 (m, 1H), 1.97-1.86 (m, 2H), 1.78 (d, 3H, J=1.0 Hz), 1.68-1.53 (m, 3H), 0.90 (d, 3H, J=6.7 Hz), 0.80-0.78 (m, 1H), 0.48 (d, 3H, J=7.0 Hz); $^{13}$C NMR (C$_6$D$_6$, 125 MHz, cryogenic probe) δ 165.7, 160.6, 145.2, 142.9, 140.4, 138.3, 134.1, 128.9, 127.9, 125.6, 125.3, 124.0, 122.0, 116.6, 110.6, 101.1, 99.4, 86.4, 79.0, 78.3, 74.4, 72.9, 69.0, 67.2, 41.3, 40.2, 38.3, 35.3, 33.5, 32.6, 32.0, 31.9, 16.2, 14.1, 13.2; high resolution mass spectrum (ES$^+$) m/z 596.2986 [(M+Na)$^+$; calcd for C$_{35}$H$_{43}$NO$_6$Na: 596.2988].

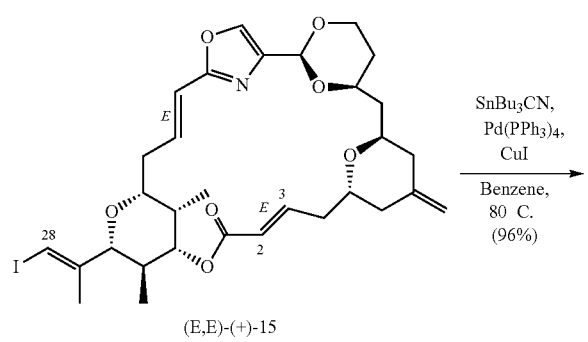

(E,E)-(+)-15

SnBu$_3$CN, Pd(PPh$_3$)$_4$, CuI

Benzene, 80 C. (96%)

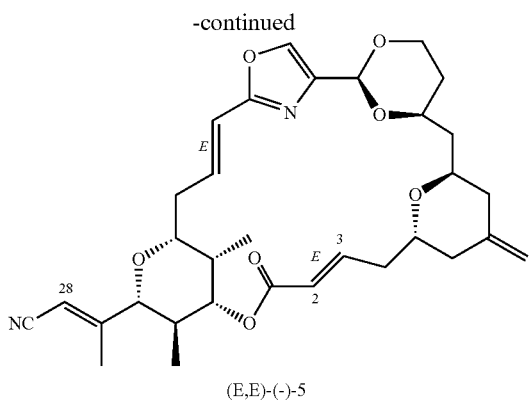

(E,E)-(−)-5

Vinyl iodide (E,E)-(+)-15 [Smith, A. B., III; Razler, T. M.; Meis, R. M.; Pettit, G. R. Org. Lett. 2006, 8, 797-799] (9.6 mg, 14.4 μmmol), copper iodide (0.9 mg, 4.72 μmmol), tetrakis(triphenylphosphine)palladium(0) (6.0 mg, 5.19 μmmol) and tri-n-butyltincyanide (5.7 mg, 18.03 μmmol) were placed in a sealed tube and anhydrous benzene (0.8 mL) added. The reaction was heated at 90° C. for 3 h. After cooling to rt, silica gel chromatography (20% to 35% EtOAc/hexanes) afforded (E,E)-(−)-5 as colorless solid (7.8 mg, 96%): $[\alpha]_D^{21}$ −2.2 (c 0.28, $C_6D_6$); $^1$H NMR (CDCl$_3$, 500 MHz) δ: 7.57 (s, 1H), 6.88 (dd, 1H, J=15.5, 8.6, 5.7 Hz), 6.65-6.59 (m, 1H), 6.27 (d, 1H, J=16.2 Hz), 5.86 (d, 1H, J=15.5 Hz), 5.49 (s, 1H), 5.32 (s, 1H), 4.83 (s, 1H), 4.84-4.81 (m, 1H), 4.78 (s, 1H), 4.23 (dd, 1H, J=11.9, 4.6 Hz), 4.10-4.06 (m, 1H), 3.76 (dt, 1H, J=12.2, 1.6 Hz), 3.79-3.75 (m, 1H), 3.65-3.62 (m, 2H), 3.57 (d, 1H, J=10.3 Hz), 2.62-2.57 (m, 1H), 2.46-2.38 (m, 2H), 2.32 (dd, 1H, J=13.1, 3.1 Hz), 2.27-2.20 (m, 1H), 2.09 (s, 3H), 2.02-1.98 (m, 2H), 1.95-1.90 (m, 4H), 1.80-1.72 (m, 1H), 1.40 (d, 1H, J=14.0 Hz), 1.34-1.30 (m, 1H), 0.93 (d, 3H, J=6.6 Hz), 0.76 (d, 3H, J=6.6 Hz); $^{13}$C NMR (CDCl$_3$, 125 MHz, cryoprobe) δ: 167.0, 161.4, 161.1, 147.3, 141.4, 139.8, 135.7, 134.8, 122.8, 119.1, 116.4, 111.6, 99.1, 95.1, 86.6, 77.8, 73.3, 70.8, 69.0, 66.9, 41.1, 40.4, 38.7, 37.4, 34.4, 32.4, 31.8, 29.9, 16.6, 13.0, 6.1, 1.2; IR (neat): 2923 (m), 2853 (m), 2218 (w), 1719 (m), 1655 (m) cm$^{-1}$; high resolution mass spectrum (ES$^+$) m/z 565.2909 [(M+H)$^+$; calcd for $C_{32}H_{41}N_2O_7$: 565.2914].

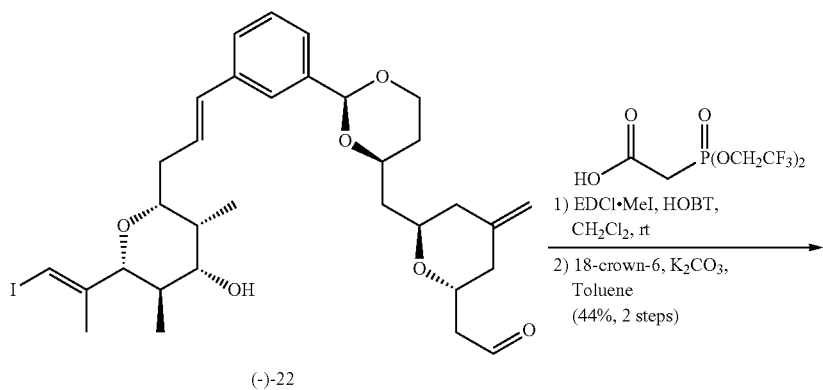

(−)-22

1) EDCl·MeI, HOBT, CH$_2$Cl$_2$, rt
2) 18-crown-6, K$_2$CO$_3$, Toluene
(44%, 2 steps)

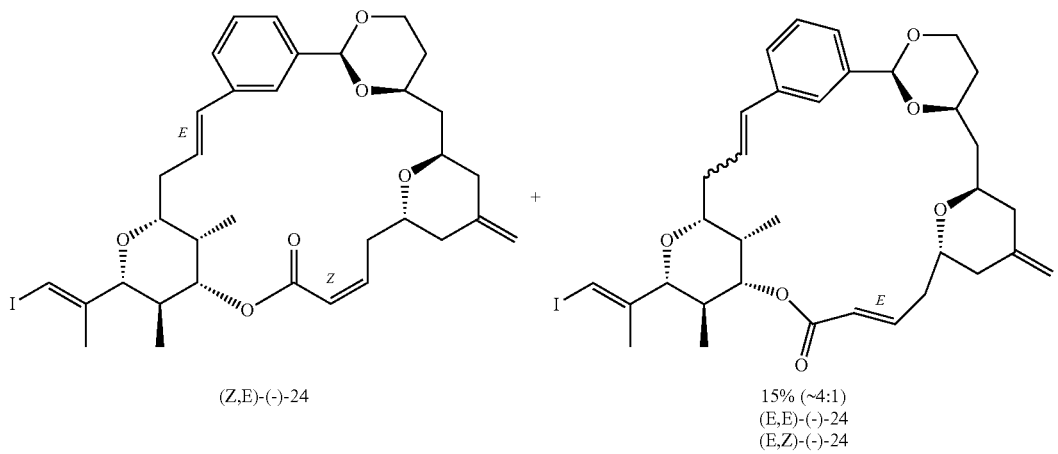

(Z,E)-(−)-24

15% (~4:1)
(E,E)-(−)-24
(E,Z)-(−)-24

Purification by preparative HPLC (eluent: acetonitrile/water) provided (E,E)-/(E,Z)-(−)-24.

(E,E)-(−)-24: $[\alpha]_D^{23}$ −8.6 (c 0.52, $C_6D_6$); $^1$H NMR ($C_6D_6$, 500 MHz) δ: 8.09 (s, 1H), 7.24-7.11 (m, 3H), 7.03-7.01 (m, 1H), 6.39 (d, 1H, J=16.2 Hz), 6.04 (d, 1H, J=16.1 Hz), 6.06 (s, 1H), 5.69 (ddd, 1H, J=16.2, 9.3, 4.7 Hz), 5.35 (s, 1H), 5.09 (dd, 1H, J=11.1, 4.5 Hz), 4.75 (s, 1H), 4.65 (s, 1H), 4.25-4.20 (m, 1H), 3.92 (dd, 1H, J=11.8, 4.9 Hz), 3.53-3.49 (m, 1H), 3.35 (d, 1H, J=10.4 Hz), 3.27-3.24 (m, 3H), 2.53-2.47 (m, 1H), 2.28-2.20 (m, 2H), 2.12-2.04 (m, 1H), 1.97-1.93 (m, 1H), 1.91-1.82 (m, 2H), 1.80-1.63 (m, 6H), 1.78 (s, 3H), 0.90 (d, 3H, J=6.8 Hz), 0.79 (d, 1H, J=13.9 Hz), 0.75 (s, 3H, J=6.5 Hz); $^{13}$C NMR ($C_6D_6$, 125 MHz) δ: 167.0, 147.3, 146.8, 142.7, 140.4, 139.5, 133.7, 129.5, 127.9, 126.7, 126.6, 124.1, 124.0, 111.3, 102.4, 87.8, 81.5, 78.6, 77.3, 74.4, 71.1, 69.5, 67.4, 41.4, 40.3, 38.4, 37.8, 36.1, 35.7, 33.5, 32.4, 19.6, 13.6, 6.2; IR (neat): 2968 (m), 2929 (m), 2851 (m), 1714 (m) cm$^{-1}$; high resolution mass spectrum (ES$^+$) m/z 697.2005 [(M+Na)$^+$; calcd for $C_{34}H_{43}O_{61}$Na: 697.2002].

(E,Z)-(−)-24: $[\alpha]_D^{21}$ −27.7 (c 0.12, CDCl$_3$); $^1$H NMR (CDCl$_3$, 500 MHz) δ: 7.40 (s, 1H), 7.28-7.26 (m, 1H), 7.16-7.14 (m, 1H), 7.00-6.94 (m, 2H), 6.62 (d, 1H, J=11.6 Hz), 6.27 (s, 1H), 5.82 (d, 1H, J=15.9 Hz), 5.52 (dt, 1H, J=11.6, 4.5 Hz), 5.41 (s, 1H), 4.84 (s, 1H), 4.78 (s, 1H), 4.67 (dd, 1H, J=10.9, 4.9 Hz), 4.21 (dd, 1H, J=11.7, 4.8 Hz), 3.94-3.87 (m, 2H), 3.76-3.71 (m, 1H), 3.62-3.58 (m, 1H), 3.59 (d, 1H, J=10.4 Hz), 3.49-3.42 (m, 1H), 2.88-2.80 (m, 1H), 2.48-2.42 (m, 1H), 2.40-2.32 (m, 2H), 2.24-2.19 (m, 3H), 2.05-1.74 (m, 6H), 1.78 (s, 3H), 1.43 (d, 1H, J=13.3 Hz), 0.66 (d, 3H, J=6.4 Hz), 0.528 (d, 3H, J=7.0 Hz); IR (neat): 2958 (m), 2923 (m), 2853 (m), 1653 (m), 1634 (m) cm$^{-1}$; high resolution mass spectrum (ES$^+$) m/z 697.1996 [M+Na]$^+$; calcd for $C_{34}H_{43}O_{61}$Na: 697.2002].

tetrakis(triphenylphosphine)palladium(0) (3.9 mg, 3.37 µmmol) and tri-n-butyltincyanide (4.7 mg, 14.87 µmmol) were placed in a sealed tube and anhydrous benzene (0.7 mL) added. The reaction was heated at 80° C. for 3.5 h. After cooling to rt, silica gel chromatography (20% EtOAc/hexanes) afforded (E,E)-(−)-6 as a colorless amorphous solid (4.1 mg, 71%); (E,Z)-(−)-6 was also isolated as a colorless amorphous solid (1.1 mg, 19%).

(E,E)-(−)-6: $[\alpha]_D^{21}$ −12.4 (c 0.2, CDCl$_3$); $^1$H NMR ($C_6D_6$, 500 MHz) δ: 8.08 (s, 1H), 7.25-7.14 (m, 3H), 7.04-7.03 (m, 1H), 6.40 (d, 1H, J=16.1 Hz), 6.04 (d, 1H, J=15.6 Hz), 5.67 (ddd, 1H, J=15.6, 9.2, 4.8 Hz), 5.35 (s, 1H), 4.99 (dd, 1H, J=11.1, 4.6 Hz), 4.76 (s, 1H), 4.65 (s, 2H), 4.24-4.21 (m, 1H), 3.91 (dd, 1H, J=11.9, 4.9 Hz), 3.51 (dt, 1H, J=12.0, 2.4 Hz), 3.33-3.21 (m, 3H), 3.03 (d, 1H, J=10.1 Hz), 2.46-2.43 (m, 1H), 2.23-2.15 (m, 2H), 2.11-2.04 (m, 1H), 1.93-1.87 (m, 2H), 1.78-1.72 (m, 4H), 1.74 (s, 3H), 1.68-1.61 (m, 3H), 0.82 (d, 3H, J=6.8 Hz), 0.78 (d, 1H, J=12.9 Hz), 0.60 (d, 3H, J=6.6 Hz); $^{13}$C NMR ($C_6D_6$, 125 MHz) δ: 167.0, 160.7, 147.7, 142.7, 140.4, 139.3, 133.9, 127.9, 126.8, 126.2, 124.0, 116.6, 111.4, 102.4, 99.3, 86.3, 78.1, 77.5, 74.4, 71.0, 69.5, 67.4, 41.4, 40.3, 38.5, 37.7, 36.0, 35.5, 33.4, 32.4, 16.2, 13.4, 6.0; high resolution mass spectrum (ES$^+$) m/z 574.3185 [(M+H)$^+$; calcd for $C_{35}H_{44}O_6$N: 574.3169].

(E,Z)-(−)-6: $[\alpha]_D^{21}$ −19 (c 0.18, CDCl$_3$); $^1$H NMR (CDCl$_3$, 500 MHz) δ: 7.40 (s, 1H), 7.30-7.22 (m, 2H), 7.17-7.15 (m, 1H), 6.98 (dt, 1H, J=15.8, 8.4 Hz), 6.64 (d, 1H, J=11.7 Hz), 5.82 (d, 1H, J=15.8 Hz), 5.51 (dt, 1H, J=11.7, 4.1 Hz), 5.48 (s, 1H), 5.29 (s, 1H), 4.84 (s, 1H), 4.78 (s, 1H), 4.68 (dd, 1H, J=11.0, 4.9 Hz), 4.20 (dd, 1H, J=10.9, 5.2 Hz), 3.94-3.87 (m, 2H), 3.76-3.70 (m, 1H), 3.62-3.58 (m, 1H), 3.52-3.46 (m, 2H), 2.88-2.81 (m, 1H), 2.48-2.46 (m, 1H), 2.40-2.32 (m, 2H), 2.26-2.17 (m, 3H), 2.02 (s, 3H), 2.03-1.73 (m, 6H), 1.42 (d, 1H, J=12.3 Hz), 0.69 (d, 3H, J=6.5 Hz), 0.28 (d, 3H, J=6.8 Hz); IR (neat): 2958 (m), 2922 (m), 2853 (m), 2222 (w), 1659 (m) cm$^{-1}$; high resolution mass spectrum (ES$^+$) m/z 574.3149 [(M+H)$^+$; calcd for $C_{35}H_{44}NO_6$: 574.3169].

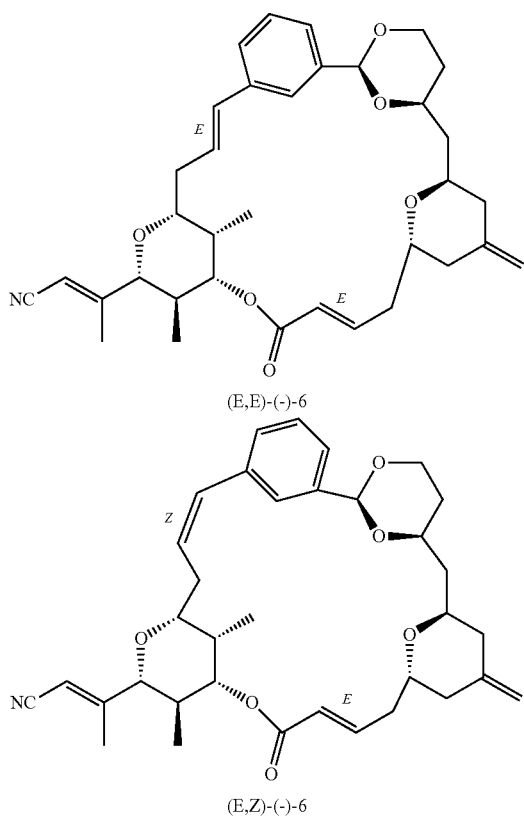

(E,E)-(−)-6

(E,Z)-(−)-6

Vinyl iodide (E,E)-/(E,Z)-(−)-24 (6.7 mg, 9.93 µmmol, 4:1 mixture of isomers), copper iodide (1.1 mg, 5.78 µmmol),

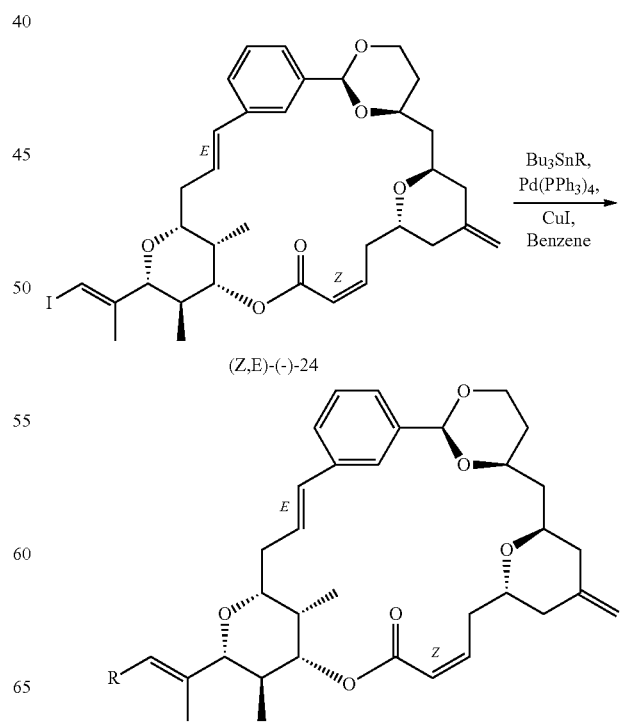

(Z,E)-(−)-24

-continued

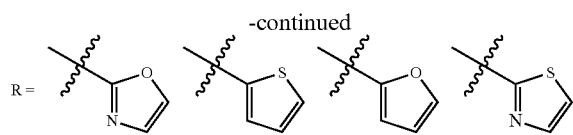

R =

Oxazole Analogue (+)-27

Vinyl iodide (−)-24 (6.1 mg, 9.04 μmmol), copper iodide (1.1 mg, 5.78 μmmol), tetrakis(triphenylphosphine)palladium(0) (3.9 mg, 3.37 μmmol) and 2-(tributylstannyl)oxazole (3 μL, 14.3 μmmol) were placed in a sealed tube and anhydrous benzene (0.6 mL) added. The reaction was heated at 80° C. for 3 h. After cooling to rt, silica gel chromatography (20% EtOAc/hexanes) afforded (+)-27 as colorless solid (4.2 mg, 76%): $[\alpha]_D^{16}$ +21.6 (c 0.40, CDCl$_3$); $^1$H NMR (CDCl$_3$, 500 MHz) δ: 7.61 (s, 1H), 7.42 (d, 1H, J=8.5 Hz), 7.32-7.23 (m, 3H), 7.18 (s, 1H), 6.47 (d, 1H, J=15.9 Hz), 6.35 (s, 1H), 6.02-5.96 (m, 2H), 5.92 (d, 1H, J=11.5 Hz), 5.49 (s, 1H), 4.85 (s, 1H), 4.70 (s, 1H), 4.62 (dd, 1H, J=11.1, 4.6 Hz), 4.32 (dd, 1H, J=12.3, 4.5 Hz), 4.18-4.16 (m, 1H), 4.05-4.01 (m, 1H), 4.00-3.94 (m, 2H), 3.64-3.60 (m, 2H), 3.30-3.23 (m, 1H), 2.51-2.42 (m, 4H), 2.39-2.37 (m, 1H), 2.26 (s, 3H), 2.11 (d, 1H, J=13.8 Hz), 2.07-1.87 (m, 5H), 1.64-1.59 (m, 1H), 1.50 (d, 1H, J=13.1 Hz), 1.00 (d, 3H, J=6.9 Hz), 0.80 (d, 3H, J=6.5 Hz); $^{13}$C NMR (CDCl$_3$, 125 MHz) δ: 165.9, 161.3, 145.2, 144.1, 141.9, 138.9, 137.8, 137.7, 133.5, 128.7, 128.3, 127.5, 125.2, 124.3, 123.3, 121.9, 115.2, 110.5, 100.7, 89.0, 79.6, 78.2, 74.2, 73.4, 68.4, 67.2, 41.4, 39.9, 37.5, 35.1, 33.0, 32.4, 31.9, 31.3, 14.5, 13.4, 6.5; IR (neat): 2956 (w), 2923 (m), 2851 (m), 1719 (m) cm$^{-1}$; high resolution mass spectrum (ES$^+$) m/z 616.3271 [(M+H)$^+$; calcd for C$_{37}$H$_{46}$NO$_7$: 616.3274].

Thiophene Analogue (+)-28

Vinyl iodide (−)-24 (3.6 mg, 5.33 μmmol), copper iodide (0.6 mg, 3.15 μmmol), tetrakis(triphenylphosphine)palladium(0) (2.2 mg, 1.90 μmmol) and 2-(tributylstannyl)thiophene (3 μL, 9.44 μmmol) were placed in a sealed tube and anhydrous benzene (0.4 mL) added. The reaction was heated at 80° C. for 3.5 h. After cooling to rt, silica gel chromatography (20% EtOAc/hexanes) afforded (+)-28 as colorless solid (2.6 mg, 76%): $[\alpha]_D^{17}$ +11.0 (c 0.26, CDCl$_3$); $^1$H NMR (CDCl$_3$, 500 MHz) δ: 7.55-7.52 (m, 1H), 7.42-7.38 (m, 2H), 7.32-7.23 (m, 2H), 7.03-7.02 (m, 2H), 6.63 (s, 1H), 6.47 (d, 1H, J=16.0 Hz), 6.02-5.96 (m, 2H), 5.93 (d, 1H, J=11.3 Hz), 5.49 (s, 1H), 4.85 (s, 1H), 4.71 (s, 1H), 4.62 (dd, 1H, J=11.5, 4.5 Hz), 4.32 (dd, 1H, J=11.5, 4.9 Hz), 4.18-4.14 (m, 1H), 4.05-4.01 (m, 1H), 4.00-3.93 (m, 2H), 3.63-3.60 (m, 2H), 3.31-3.24 (m, 1H), 2.52-2.42 (m, 4H), 2.38-2.36 (m, 1H), 2.10 (d, 1H, J=13.5 Hz), 2.04 (s, 3H), 2.02-1.89 (m, 5H), 1.64-1.57 (m, 1H), 1.50 (d, 1H, J=13.4 Hz), 1.00 (d, 3H, J=6.9 Hz), 0.79 (d, 3H, J=6.6 Hz); $^{13}$C NMR (CDCl$_3$, 125 MHz) δ: 166.0, 143.9, 141.8, 140.5, 138.9, 137.8, 134.2, 133.4, 128.7, 127.8, 127.5, 127.0, 125.5, 125.4, 124.3, 123.3, 123.0, 121.9, 110.5, 100.7, 89.9, 79.8, 78.0, 74.2, 73.4, 68.4, 67.2, 41.4, 39.9, 37.5, 35.2, 33.0, 32.4, 31.9, 31.3, 14.1, 13.7, 6.6; IR (neat): 2923 (m), 2849 (m), 1715 (m) cm$^{-1}$; high resolution mass spectrum (ES$^+$) m/z 631.3107 [(M+H)$^+$; calcd for C$_{38}$H$_{47}$O$_6$S: 631.3093].

Furan Analogue (+)-26

Vinyl iodide (−)-24 (5.3 mg, 7.86 μmmol), copper iodide (1.1 mg, 5.78 μmmol), tetrakis(triphenylphosphine)palladium(0) (3.6 mg, 3.11 μmmol) and 2-(tributylstannyl)furan (3 μL, 9.52 μmmol) were placed in a sealed tube and anhydrous benzene (0.5 mL) added. The reaction was heated at 80° C. for 3 h. After cooling to rt, silica gel chromatography (20% EtOAc/hexanes) afforded (+)-27 as colorless solid (4.3 mg, 90%): $[\alpha]_D^{17}$ +3.6 (c 0.28, C$_6$D$_6$); $^1$H NMR (C$_6$D$_6$, 500 MHz) δ: 7.72 (s, 1H), 7.64 (d, 1H, J=7.8 Hz), 7.10-7.08 (m, 2H), 7.04 (bs, 1H), 6.44 (d, 1H, J=15.9 Hz), 6.33 (s, 1H), 6.14 (s, 2H), 5.97 (dt, 1H, J=15.9, 7.8 Hz), 5.88 (d, 1H, J=11.4 Hz), 5.62 (dt, 1H, J=11.4, 4.6 Hz), 5.33 (s, 1H), 4.84 (s, 1H), 4.78 (dd, 1H, J=11.3, 4.1 Hz), 4.75 (s, 1H), 4.23-4.19 (m, 1H), 4.00-3.94 (m, 2H), 3.67-3.60 (m, 1H), 3.54-3.48 (m, 2H), 3.45-3.42 (m, 1H), 3.43 (d, 1H, J=9.8 Hz), 2.61-2.59 (m, 1H), 2.53-2.43 (m, 4H), 2.27 (dd, 1H, J=12.9, 4.6 Hz), 2.09 (s, 3H), 2.07-2.04 (m, 1H), 1.99-1.87 (m, 4H), 1.66-1.63 (m, 1H), 1.60-1.55 (m, 1H), 1.09 (d, 3H, J=6.7 Hz), 0.79 (d, 3H, J=6.7 Hz); $^{13}$C NMR (CDCl$_3$, 125 MHz) δ: 166.0, 152.9, 143.9, 141.8, 141.7, 138.9, 137.8, 134.7, 133.4, 128.7, 127.5, 125.4, 124.3, 123.3, 121.9, 118.4, 111.4, 110.5, 109.7, 100.7, 89.6, 79.8, 78.0, 74.2, 73.4, 68.4, 67.2, 41.4, 39.9, 37.5, 35.2, 33.0, 32.3, 31.9, 31.3, 14.0, 13.6, 6.6; IR (neat): 2922 (m), 2851 (m), 1719 (s), 1642 (w) cm$^{-1}$; high resolution mass spectrum (ES$^+$) m/z 637.3158 [(M+Na)$^+$; calcd for C$_{38}$H$_{46}$O$_7$Na: 637.3141].

Thiazole Analogue (+)-29

Vinyl iodide (−)-24 (4.6 mg, 6.82 μmmol), copper iodide (0.9 mg, 4.72 μmmol), tetrakis(triphenylphosphine)palladium(0) (3.5 mg, 3.03 μmmol) and 2-tributylstannylthiazole (3 μL, 9.54 μmmol) were placed in a sealed tube and anhydrous benzene (0.5 mL) added. The reaction was heated at 80° C. for 3 h. After cooling to rt, silica gel chromatography (20% EtOAc/hexanes) afforded (+)-29 as colorless solid (3.2 mg, 73%): $[\alpha]_D^{16}$ +15.4 (c 0.32, CDCl$_3$); $^1$H NMR (CDCl$_3$, 500 MHz) δ: 7.85 (d, 1H, J=3.2 Hz), 7.42 (s, 1H, J=7.7 Hz), 7.33-7.23 (m, 4H), 6.79 (s, 1H), 6.47 (d, 1H, J=16.2 Hz), 6.02-5.96 (m, 2H), 5.92 (d, 1H, J=11.0 Hz), 5.49 (s, 1H), 4.85 (s, 1H), 4.71 (s, 1H), 4.63 (dd, 1H, J=11.5, 4.4 Hz), 4.32 (dd, 1H, J=11.1, 4.4 Hz), 4.19-4.15 (m, 1H), 4.06-4.01 (m, 1H), 4.00-3.94 (m, 2H), 3.67 (d, 1H, J=10.4 Hz), 3.66-3.62 (m, 1H), 3.31-3.23 (m, 1H), 2.52-2.38 (m, 5H), 2.20 (s, 3H), 2.12-2.87 (m, 6H), 1.64-1.59 (m, 1H), 1.50 (d, 1H, J=13.3 Hz), 1.00 (d, 3H, J=6.9 Hz), 0.81 (d, 3H, J=6.4 Hz); $^{13}$C NMR (CDCl$_3$, 125 MHz) δ: 165.8, 164.8, 145.4, 144.0, 143.1, 141.8, 141.5, 138.8, 133.4, 128.6, 127.4, 125.1, 124.2, 123.2, 122.9, 121.8, 119.0, 110.4, 100.6, 89.3, 79.5, 78.0, 74.1, 73.3, 68.3, 67.1, 41.3, 39.8, 37.4, 35.0, 32.9, 32.4, 31.8, 31.2, 14.8, 13.5, 6.5; IR (neat): 2921 (m), 2853 (m), 1723 (m) cm$^{-1}$; high resolution mass spectrum (ES) m/z 632.3058 [(M+H)$^+$; calcd for $C_{37}H_{46}NO_6S$: 632.3046].

What is claimed:

1. A compound of formula I:

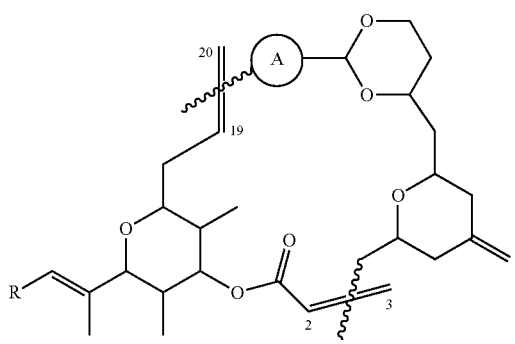

wherein ring A is aryl or a 5- or 6-membered heteroaryl optionally substituted with one or more of halogen, —OH, or —$C_{1-6}$alkyl; and R is —CN, a 5- or 6-membered heteroaryl, or halogen;

or a pharmaceutically acceptable salt form thereof;

with the proviso that if A is oxazolyl, then R is —CN or a 5- or 6-membered heteroaryl.

2. The compound of claim 1, wherein ring A is aryl.

3. The compound of claim 1, wherein ring A is phenyl.

4. The compound of claim 1, wherein ring A is a 5-membered heteroaryl.

5. The compound of claim 1, wherein ring A is oxazolyl.

6. The compound of claim 1, wherein ring A is thiazolyl.

7. The compound of claim 1, wherein R is —CN.

8. The compound of claim 1, wherein R is oxazolyl.

9. The compound of claim 1, wherein R is thiazolyl.

10. The compound of claim 1, wherein R is iodo.

11. The compound of claim 1, wherein the geometry of the C(2-3) double bond is Z.

12. The compound of claim 1, wherein the geometry of the C(2-3) double bond is E.

13. The compound of claim 1, wherein the geometry of the C(19-20) double bond is Z.

14. The compound of claim 1, wherein the geometry of the C(19-20) double bond is E.

15. The compound of claim 1, wherein the geometry of the C(2-3) double bond is Z and the geometry of the C(19-20) double bond is E.

16. The compound of claim 1, wherein the geometry of the C(2-3) double bond is E and the geometry of the C(19-20) double bond is E.

17. The compound of claim 1, wherein the geometry of the C(2-3) double bond is E and the geometry of the C(19-20) double bond is Z.

18. The compound of claim 1 that is:

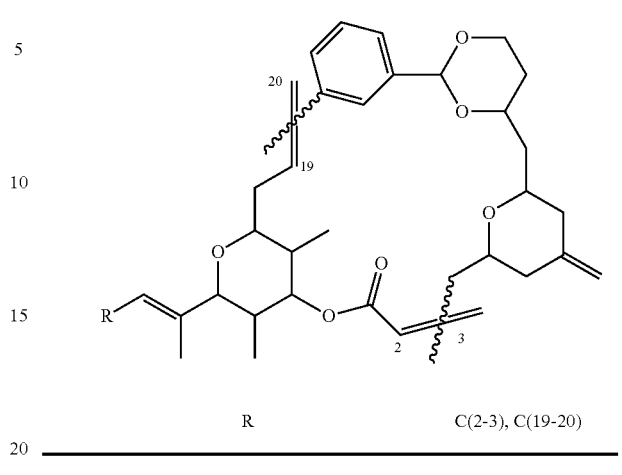

| R | C(2-3), C(19-20) |
|---|---|
| —CN | (Z, E) |
| —I | (Z, E) |
| —I | (E, E) |
| —I | (E, Z) |
| —CN | (E, E) |
| —CN | (E, Z) |
| 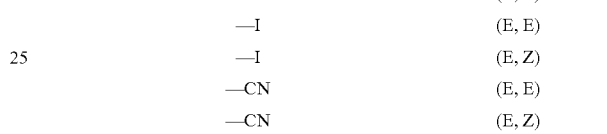 | (Z, E) |
| 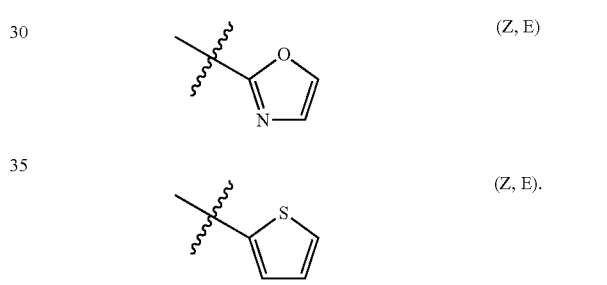 | (Z, E). |

19. The compound of claim 1 that is:

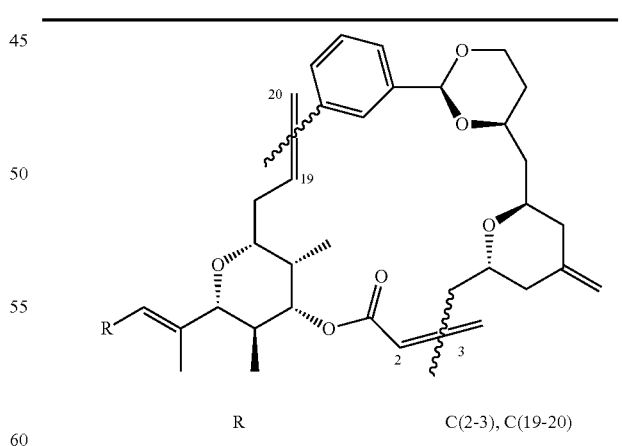

| R | C(2-3), C(19-20) |
|---|---|
| —CN | (Z, E) |
| —I | (Z, E) |
| —I | (E, E) |
| —I | (E, Z) |
| —CN | (E, E) |
| —CN | (E, Z) |

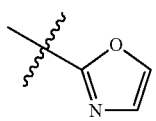 [SMILES: *c1ncco1] (Z, E)

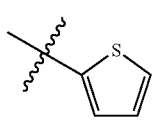 [SMILES: *c1cccs1] (Z, E).

20. The compound of claim 1 that is:

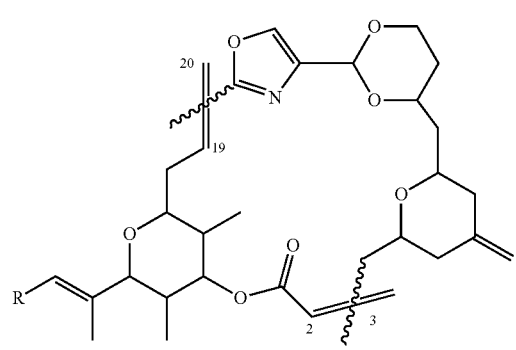

| R | C(2-3), C(19-20) |
|---|---|
| —CN | (Z, E) |
| —CN | (E, E). |

21. The compound of claim 1 that is:

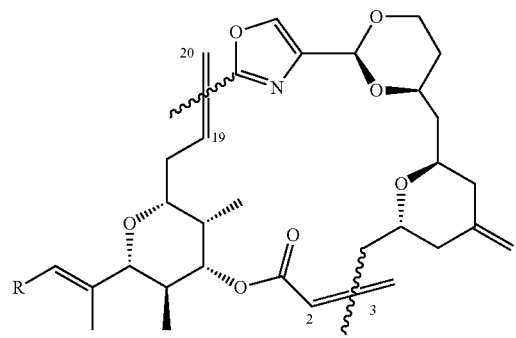

| R | C(2-3), C(19-20) |
|---|---|
| —CN | (Z, E) |
| —CN | (E, E). |

22. A method of treating a *Candida albicans* infection in a patient comprising administering to the patient a therapeutically effective amount of a compound that is

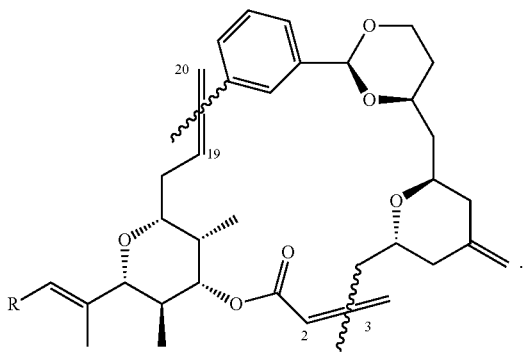

| R | C(2-3), C(19-20) |
|---|---|

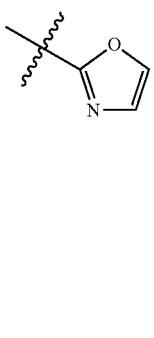 (Z, E)

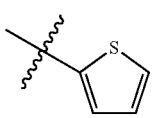 [SMILES: *c1cccs1] (Z, E)

or

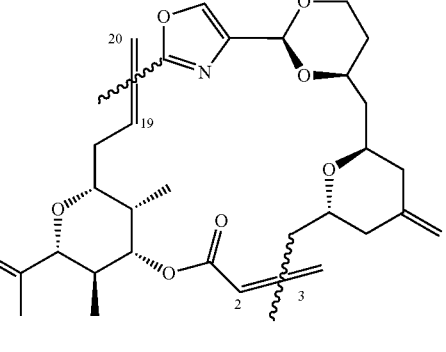

| R | C(2-3), C(19-20) |
|---|---|
| —CN | (Z, E) |
| —CN | (E, E). |

23. A method of treating breast cancer in a patient comprising administering to the patient a therapeutically effective amount of the following compound:

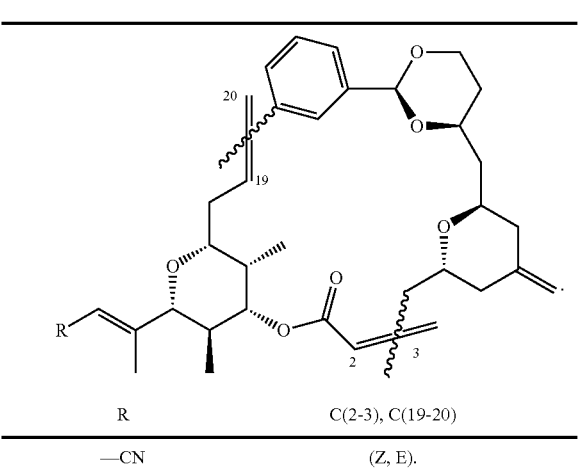
| R | C(2-3), C(19-20) |
|---|---|
| —CN | (Z, E). |
24. A method of treating colon cancer in a patient comprising administering to the patient a therapeutically effective amount of a compound that is:
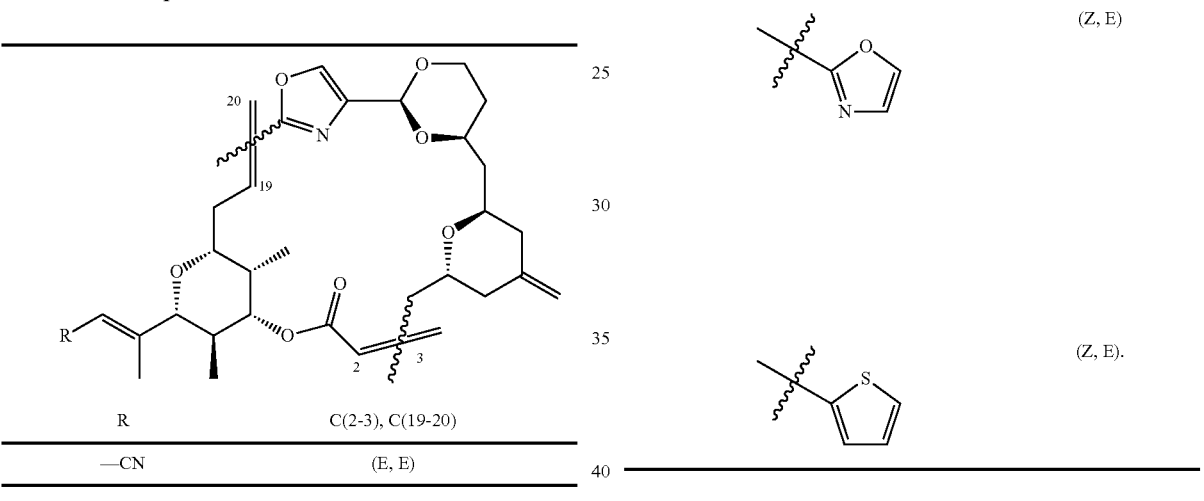
| R | C(2-3), C(19-20) |
|---|---|
| —CN | (E, E) |
or
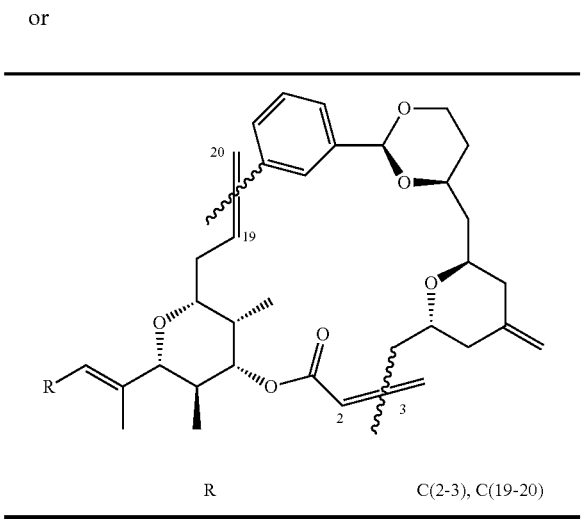
* * * * *

UNITED STATES PATENT AND TRADEMARK OFFICE
CERTIFICATE OF CORRECTION

PATENT NO. : 8,957,097 B2
APPLICATION NO. : 13/386783
DATED : February 17, 2015
INVENTOR(S) : Amos B. Smith, III et al.

Page 1 of 1

It is certified that error appears in the above-identified patent and that said Letters Patent is hereby corrected as shown below:

In the specification

Column 1,
Lines 7-11, delete "The research carried out in this application was supported, in part, by grants from the National Institute of Health (National Cancer Institute) through grants CA-19033 and CA-122256. Pursuant to 35 U.S.C. 202, the government may have rights in any patent issuing from this application." and insert -- This invention was made with government support under grant number CA-019033 and CA122256 awarded by National Institute of Health. The government has certain rights in the invention. --.

Column 46,
Line 5, delete "$C_{32}H_4ON_2NaO_7$:" and insert -- $C_{32}H_{40}N_2NaO_7$: --.

Column 51,
Line 14, delete "$C_{41}H_{56}O_{81}$:" and insert -- $C_{41}H_{56}O_8I$: --.

Column 52,
Line 67, delete "$C_{32}H_{43}O_{61}Na$:" and insert -- $C_{32}H_{43}O_6INa$: --.

Column 53,
Lines 66-67, delete "$C_{34}H_{43}O_{61}Na$:" and insert -- $C_{34}H_{43}O_6INa$: --.

Column 57,
Line 18, delete "$C_{34}H_{43}O_{61}Na$:" and insert -- $C_{34}H_{43}O_6INa$: --.
Line 31, delete "$C_{34}H_{43}O_{61}Na$:" and insert -- $C_{34}H_{43}O_6INa$: --.

Signed and Sealed this
Twenty-seventh Day of October, 2015

Michelle K. Lee
*Director of the United States Patent and Trademark Office*